United States Patent [19]
Oinuma et al.

[11] Patent Number: 6,051,705
[45] Date of Patent: Apr. 18, 2000

[54] SUBSTITUTED THIAZOLO[3,2-A]AZEPINE DERIVATIVES

[75] Inventors: Hitoshi Oinuma; Shinji Suda; Naoki Yoneda, all of Ibaraki; Makoto Kotake, Chiba; Masanori Mizuno, Ibaraki; Tomohiro Matsushima, Ibaraki; Yoshio Fukuda, Ibaraki; Mamoru Saito, Ibaraki; Toshiyuki Matsuoka, Ibaraki; Hideyuki Adachi, Ibaraki; Masayuki Namiki, Ibaraki; Takeshi Sudo, Ibaraki; Kazutoshi Miyake, Ibaraki; Makoto Okita, Ibaraki, all of Japan

[73] Assignee: Eisai Co., Ltd., Tokyo, Japan

[21] Appl. No.: 09/085,729

[22] Filed: May 27, 1998

Related U.S. Application Data

[62] Division of application No. 08/612,864, filed as application No. PCT/JP95/01139, Jun. 7, 1995, Pat. No. 5,789,403.

[30] Foreign Application Priority Data

| Jul. 18, 1994 | [JP] | Japan | 6-165481 |
| Aug. 24, 1994 | [JP] | Japan | 6-199180 |
| Dec. 9, 1994 | [JP] | Japan | 6-306468 |

[51] Int. Cl.[7] ............ C07D 513/04; C07D 277/06; C07D 211/60
[52] U.S. Cl. .............................. 540/521; 540/523
[58] Field of Search ................................ 540/521, 523

[56] References Cited

FOREIGN PATENT DOCUMENTS

WO 94/10193  5/1994  WIPO.

*Primary Examiner*—Mukund J. Shah
*Assistant Examiner*—Deepak R. Rao
*Attorney, Agent, or Firm*—Flynn, Thiel, Boutell & Tanis, P.C.

[57] ABSTRACT

The present invention relates to a substituted thiazolo[3,2-a] azepine derivative having inhibitory activity against angiotensin I converting enzyme and neutral endpeptidase and is represented by the following general formula (I):

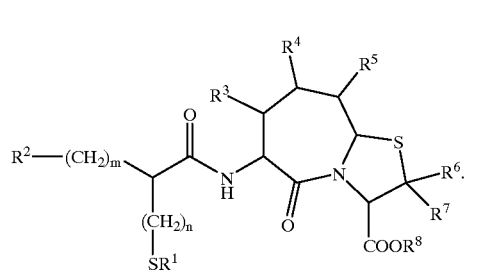

10 Claims, No Drawings

SUBSTITUTED THIAZOLO[3,2-A]AZEPINE DERIVATIVES

This is a division of Ser. No. 08/612,864, filed Mar. 11, 1996 now U.S. Pat. No. 5,789,403 which is a 371 of PCT/JP95/01139 filed Jun. 7, 1995.

FIELD OF THE INVENTION

The present invention relates to a novel substituted thiazolo[3,2-a]azepine derivative or a pharmacologically acceptable salt thereof and a process for the preparation thereof. More particularly, the present invention relates to a novel substituted thiazolo[3,2-a]azepine derivative or a pharmacologically acceptable salt thereof which is useful as a medicament and an industrially advantageous process for the preparation of said derivative.

DESCRIPTION OF THE RELATED ART

In recent years, inhibitors against neutural endpeptidase (NEP-24, 11, hereinafter abbreviated to NEP) and angiotensin I converting enzyme (hereinafter abbreviated to ACE) have been noted as new heart failure remedies.

Arterial natriuretic peptide (hereinafter abbreviated to ANP) is a hormone present in the living body, which exhibits not only potent hydrouretic and natriuretic activities and a vasodilating activity but also an inhibitory activity against the liberation of norepinephrine due to depression of sympathetic nerve, an activity of inhibiting the secretion of renin from the kidney and an activity of inhibiting the secretion of aldosterone from the adrenal gland, and, further, an activity of lowering perfusion by the enhancement of venous water permeability and so forth. The activities of ANP to patients suffering from, for example, congestive heart failure accompanied with increased preload is believed to be preferable in treating not only heart failure but also hypertension.

However, there is a problem that the clinical use of ANP is now limited to acute stages since ANP is a peptide, and therefore it cannot be administered orally and is poor in metabolic stability. Further, it has also been reported that the activities of ANP lower when it is administered for a long period of time. Accordingly, great care must be taken in the use thereof.

After due consideration of the above characteristics of ANP, those which have recently been noted as ANP-related preparations for oral administration are neutural endpeptidase inhibitors (hereinafter abbreviated to NEP inhibitors) described above. It has been reported that when administered to a patient with heart failure, an NEP inhibitor increases the blood ANP concentration to exhibit a natriuretic activity. However, the NEP inhibitors of the prior art hardly acted on cardiac blood behavior. and, therefore, decreases in preload and afterload were not clearly exhibited.

On the other hand, ACE inhibitors useful as vasodilators inhibit the formation of angiotensin (II) (hereinafter abbreviated to AT-II) which is a heart failure exacerbating factor, and thereby they exhibit significant improvement in NYHA disease severity and enhancement in tolerance to movement in chronic heart failure, and thus the usefulness thereof including their effects of prolonging life has been proved. However, the effective ratio of the ACE inhibitors of the prior art to patients are not always high and the efficacy of each of the inhibitors varies among patients. Further, there has been pointed out a problem, for example, that the inhibitors cause side effects such as hypotension, so that the administration of them to patients with renal hypofunction must be restricted.

As described above, NEP inhibitors and ACE inhibitors are noted as new heart failure remedies, but the NEP inhibitors and ACE inhibitors of the prior art have their limits in usefulness. Therefore, the development of a medicament having both the merits of an NEP inhibiting activity and an ACE inhibiting activity has been eagerly expected.

Japanese Patent Publication-A No. 6-56790 discloses the following compounds exhibiting NEP inhibiting activity and ACE inhibiting activity:

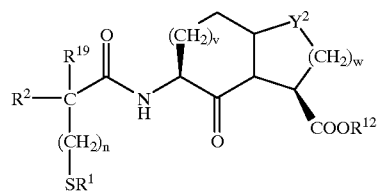

(wherein R1 represents hydrogen, R3—CO— or R18—S—; R2 and R19 each independently represent hydrogen, alkyl, cycloalkyl-(CH2)m—, substituted alkyl, aryl-(CH2)m—, substituted aryl-(CH2)m— or heteroaryl-(CH3)m—; n is 0 or 1 with the proviso that n must be 0 when both R2 and R19 are other than hydrogen; m is 0 or an integer of 1 to 6; R3 represents alkyl, substituted alkyl, cycloalkyl-(CH2)m—, aryl-(CH2)m—, substituted aryl-(CH2)m— or heteroaryl-(CH2)m—; R18 represents alkyl, substituted alkyl, cycloalkyl-(CH2)m—, aryl-(CH2)m—, substituted aryl-(CH2)m— or heteroaryl-(CH2)m—; R12 represents hydrogen, alkyl, substituted alkyl, aryl-(CH2)m—, substituted aryl-(CH2)m—, heteroaryl-(CH2)m—,

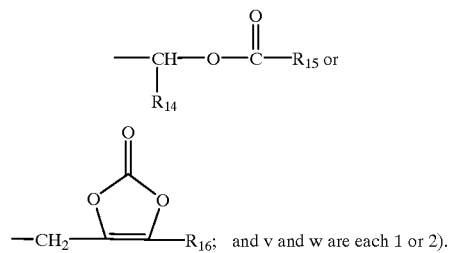

and v and w are each 1 or 2).

However, these compounds are different from the compounds of the present invention in structure, further, both the NEP inhibiting activity and ACE inhibiting activity of them are too poor to satisfy the potencies which have hitherto been required, and, furthermore, the compounds are problematic in their efficacy in oral administration. Therefore, the clinical use of them is limited. Incidentally, WO 94/10193 also discloses similar compounds to those disclosed in Japanese Patent Publication-A No. 6-56790.

Under these circumstances as described above, the present inventors have started their studies to find a medicament which exhibits excellent inhibitory activity against both NEP and ACE and can give high efficacy when administered through any route. As a result, they have found that the above object can be attained by the inventive compounds and thus being accomplished the present invention.

DISCLOSURE OF THE INVENTION

The present invention is a substituted thiazolo[3,2-a] azepine derivative represented by the following general formula (I) or a pharmacologically acceptable salt thereof:

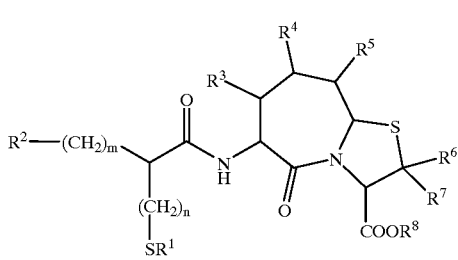

(I)

(wherein $R^1$ represents a hydrogen atom or a protecting group of a thiol group; $R^2$ represents a hydrogen atom, a lower alkyl group, an aryl group which may have a substituent, a heteroaryl group which may have a substituent, a lower alkoxy group or a lower alkylthio group; $R^3$, $R^4$ and $R^5$ are the same or different from one another and each represent a hydrogen atom, a lower alkyl group, a lower alkoxy group, a lower alkylthio group, an aryl group which may have a substituent or a heteroaryl group which may have a substituent, or, alternatively, two of $R^3$, $R^4$ and $R5$ which are adjacent to each other may form a ring together with the carbon atoms to which they are bonded, with the proviso that the case wherein all of $R^3$, $R^4$ and $R^5$ are hydrogen atoms is excepted;

$R^6$ and $R^7$ are the same or different from each other and each represent a hydrogen atom or a lower alkyl group; $R^8$ represents a hydrogen atom or a protecting group of a carboxyl group; and n and m are each independently 0, or 1 or 2).

In the above definitions, the lower alkyl group included in the definitions of $R^2$, $R^3$, $R^4$, $R^5$, $R^6$ and $R^7$ represents a linear or branched alkyl group having 1 to 6 carbon atoms. Examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, a 1,2,2-trimethylpropyl group, 1-ethyl-1-methylpropyl, 1-ethyl-2-methylpropyl and the like. Among them, preferred are a methyl group, an ethyl group, an n-propyl group, an isopropyl group, an n-butyl group, an isobutyl group and a sec-butyl group.

The lower alkoxy group included in the definitions of $R^2$, $R^3$, $R^4$ and $R^5$ is an alkoxy group having 1 to 6 carbon atoms, and represents, for example, a methoxy group, an ethoxy group, an n-propoxy group or the like.

The lower alkylthio group included in the definitions of $R^2$, $R^3$, $R^4$ and $R^5$ is an alkylthio group having 1 to 6 carbon atoms, and represents, for example, a methylthio group, an ethylthio group, an n-propylthio group or the like.

In the aryl group which may have a substituent included in the definitions of $R^2$, $R^3$, $R^4$ and $R^5$, the aryl represents phenyl, 1-naphthyl, 2-naphthyl, anthracenyl or the like.

In the heteroaryl group which may have a substituent included in the definitions of $R^2$, $R^3$, $R^4$ and $R^5$, the heteroaryl represents a ring which is composed of 3 to 8 members, preferably 5 or 6 members and which has 1 to 4 heteroatoms such as a nitrogen atom, a sulfur atom or an oxygen atom.

While, in "aryl group which may have a substituent" and "heteroaryl group which may have a substituent" included in the definitions of $R^2$, $R^3$, $R^4$ and $R^5$, the "substituent" may include lower alkyl groups such as methyl, ethyl, n-propyl and t-butyl; halogen atoms such as a fluorine atom, a chlorine atom, a bromine atom and an iodine atom; lower alkoxy groups such as methoxy, ethoxy, n-propoxy and t-butoxy; a nitro group; an amino group which may be mono- or di-substituted; and the like. With these substituents, 1 to 3 substitution(s) is(are) conducted.

The protecting group of a thiol group included in the definition of $R^1$ includes, for example, lower alkyl groups such as methyl, ethyl, n-propyl and t-butyl; acyl groups exemplified by groups derived from aliphatic saturated monocarboxylic acids such as an acetyl group, a propionyl group, a butyryl group, a pivaloyl group, a palmitoyl group and a stearoyl group; groups derived from aliphatic unsaturated carboxylic acids such as an acryloyl group, a propioloyl group, a methacryloyl group, a crotonoyl group and an oleoyl group; groups derived from carbocyclic carboxylic acids such as a benzoyl group, a naphthoyl group, a toluoyl group, an apotoyl group and a cinnamoyl group; groups derived from carbocyclic carboxylic acids such as a furoyl group, a thenoyl group, a nicotinoyl group and an isonicotinoyl group; acyl groups including, as examples thereof, groups derived from hydroxycarboxylic acids or alkoxycarboxylic acids such as a glycoloyl group, a lactoyl group, a glyceroyl group, a maloyl group, a tartaroyl group, a benziloyl group, a salicyloyl group, an anisoyl group, a vanilloyl group and a piperonyloyl group; aryl groups such as phenyl and naphthyl; heteroaryl groups such as furoyl, pyridyl and thienyl; arylalkyl groups such as benzyl; heteroarylalkyl groups such as a furoylmethyl group, a thienylmethyl group and a pyridylmethyl group; and the like.

The protecting group of a carboxyl group included in the definition of $R^8$ represents a lower alkyl group such as methyl, ethyl, n-propyl and t-butyl; an arylalkyl group such as benzyl, 1-naphthylmethyl and 2-naphthylethyl; a heteroaryl alkyl group such as 2-pyridylmethyl, 3-pyridylpropyl and 2-thienylethyl; or the like. In short, it may be any one as long as it leaves in vivo to give a carboxyl group.

In "two substituents which are adjacent to each other may form a ring together with the carbon atoms to which they are bonded" among the definitions of $R^3$, $R^4$ and $R^5$, the ring formed is preferably a ring which is composed of 5 to 8 members.

In addition, the pharmacologically acceptable salts include not only inorganic salts such as a hydrochloride, a sulfate and a nitrate, but also organic salts such as a maleate, a citrate and an acetate, and salts with alkali metals such as a sodium salt and a potassium salt; and, further, salts with amino acids such as an aspartate and a glutamate.

The compounds of the present invention have excellent inhibitory activities against both NEP and ACE. The compounds represented by the following general formula (I') are the most desirable ones among those of the present invention, because they exhibit high bioavailability and give excellent efficacy, even when administered orally:

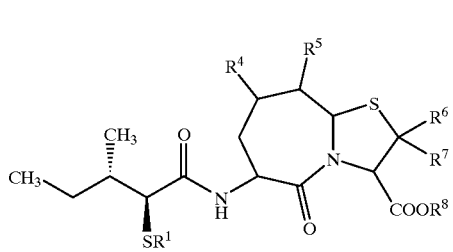
(I')

(wherein R1 represents a hydrogen atom or a protecting group of a thiol group; $R^4$ and $R^5$ may be the same or different from each other and each represent a hydrogen atom, a lower alkyl group, a lower alkoxyl group, a lower alkylthio group, an aryl group which may have a substituent or a heteroaryl group which may have a substituent, or alternatively, among $R^4$ and $R^5$, two substituents which are adjacent to each other may form a ring together with the carbon atoms to which they are bonded, with the proviso that the case wherein both $R^4$ and $R^5$ are hydrogen atoms is excepted, and, in particular, those wherein $R^4$ is a hydrogen atom and $R^5$ is a lower alkyl group are preferred, and the lower alkyl group in this case is preferably a methyl group;

$R^6$ and $R^7$ may be the same or different from each other and each represent a hydrogen atom or a lower alkyl group, with the case wherein both $R^6$ and $R^7$ are hydrogen atoms being most preferable; and $R^8$ represents a hydrogen atom or a protecting group of a carboxyl group).

Among the compounds (I) of the present invention, the most desirable compounds are represented by the following general formula (A):

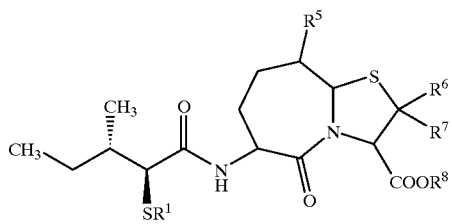
(A)

(wherein $R^1$ represents a hydrogen atom or a protecting group of a thiol group; $R^5$ represents a lower alkyl group, a lower alkoxyl group, a lower alkylthio group, an aryl group which may have a substituent or a heteroaryl group which may have a substituent, preferably a lower alkyl group, most preferably a methyl group;

$R^6$ and $R^7$ may be the same or different from each other and each represent a hydrogen atom or a lower alkyl group, with the case wherein both $R^6$ and $R^7$ are hydrogen atoms being most preferable; and $R^8$ represents a hydrogen atom or a protecting group of a carboxyl group, most preferably a hydrogen atom).

Further, the most desirable compounds among the compounds (A) of the present invention are represented by the following general formula (A'):

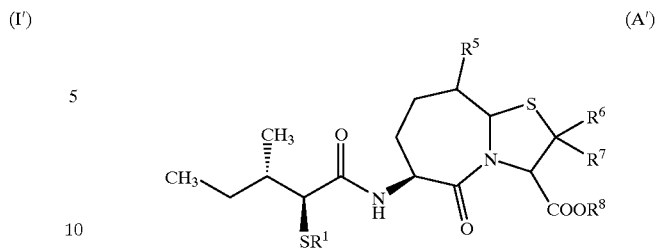
(A')

(wherein $R^1$ represents a hydrogen atom or a protecting group of a thiol group, preferably a hydrogen atom or an acetyl group; $R^5$ may be the same or different from each other and represents a lower alkyl group, a lower alkoxyl group, a lower alkylthio group, an aryl group which may have a substituent or a heteroaryl group which may have a substituent;

$R^6$ and $R^7$ may be the same or different from each other and each represent a hydrogen atom or a lower alkyl group, with the case wherein both of them are hydrogen atoms being most preferable; and $R^8$ represents a hydrogen atom or a protecting group of a carboxyl group, with the case wherein it is a hydrogen atom being most preferable).

Among the compounds (A') of the present invention, the most preferable compounds are those represented by the following two formulae which correspond to those wherein $R^5$ is a methyl group in formula (A').

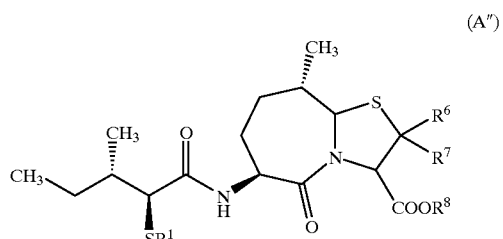
(A")

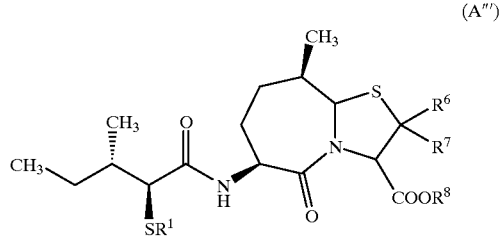
(A''')

The following two compounds, wherein all of $R^1$, $R^6$ and $R^7$ in these formulae are hydrogen atoms, are the most desirable compounds in the present invention.

Among them, the compounds wherein $R^8$ is a hydrogen atom are as follows.

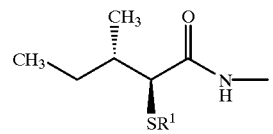

The one group of preferable compounds described above are compounds obtained by introducing a (2S, 3S)-3-methyl-2-thiopentanamido group into a thiazolo[3,2-a] azepine skeleton at position 6, and compounds having a substituent such as a lower alkyl group on a thiazolo[3,2-a]azepine skeleton at position 9. Although the abovementioned Japanese Patent Publication-A No. 6- and EP as prior art propose compounds having a thiazolo[3,2-a]azepine skeleton, in the compounds disclosed therein, every substituent present on the thiazolo[3,2-a]azepine skeleton at position 6 is mostly a benzyl group, and they do not disclose a group in the present invention which has a specific steric structure, i.e.,

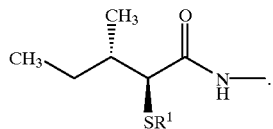

The present inventors have conducted the introduction of a (2S, 3S)-3-methyl-2-thiopentanamido group having a specific configuration to a thiazolo[3,2-a]azepine ring at position 6 based on entirely different ideas and have accidentally found that such introduction can give a compound which is excellent as a dual inhibitor against both NEP and ACE as compared with those disclosed in the prior art described above. The present invention has been accomplished on the basis of this finding.

Further, the present invention are compounds obtained by introducing a lower alkyl group (most desirably a methyl group) into the thiazolo[3,2-a]-azepine ring at position 9.

Accordingly, the present invention has been accomplished on the basis of an entirely new concept wherein the superior compounds (I) of the present invention each have a thiazolo[3,2-a]azepine ring, the position 6 thereof being substituted with

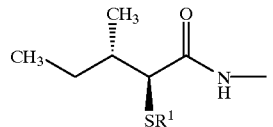

having a specific configuration, and position 9 thereof is substituted with a lower alkyl group such as a methyl group. By the introduction of this new concept, they have succeeded in obtaining compounds of the present invention which are excellent dual inhibitors.

Namely, the superior compounds of the compounds of the present invention have such characteristics that they have each not only an excellent dual inhibitory activity but also an improved bioavailability and that they exhibit an excellent effect also in oral administration, as compared with compounds disclosed in the prior art.

Of these, the following compounds are the most desirable ones.

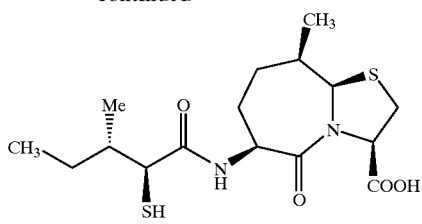

Although the compounds of the present invention can be prepared by a known process or a combination of known processes, there have been problems in that the starting compounds are expensive and that the operation was complicated. Therefore, the present inventors have studied to find a process for industrially advantageously preparing the compounds of the present invention. As a result, they have found the preparation processes which will be described below.

Preparation process 1

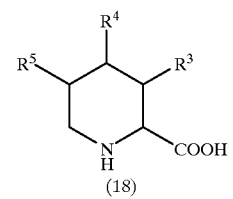

(18)

1st step | N-acylation

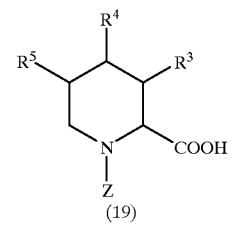

(19)

2nd step | esterification

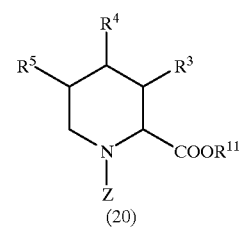

(20)

3rd step | electrolytic oxidation

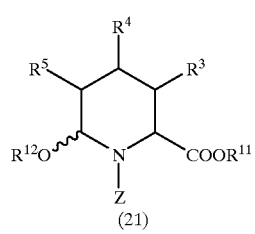

(21)

-continued
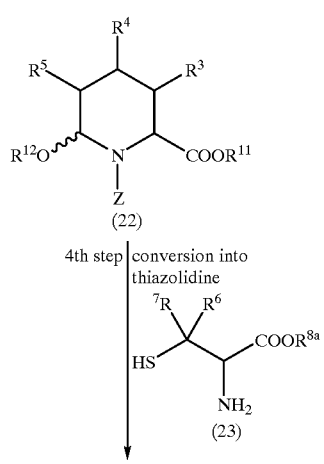
(22)
4th step | conversion into thiazolidine
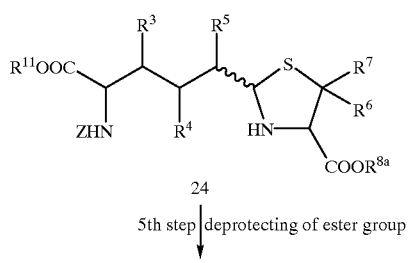
(23)
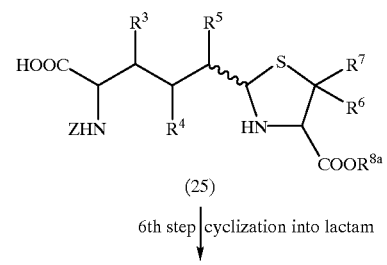
24
5th step | deprotecting of ester group
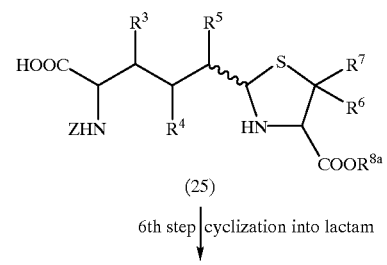
(25)
6th step | cyclization into lactam
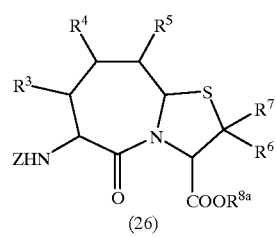
(26)
7th step | deprotecting of amino group
-continued
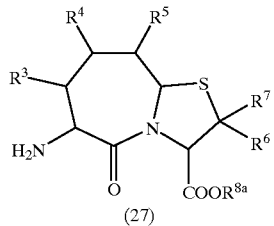
(27)
8th step | amidation
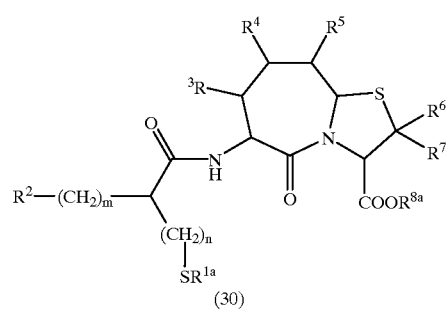
(29)
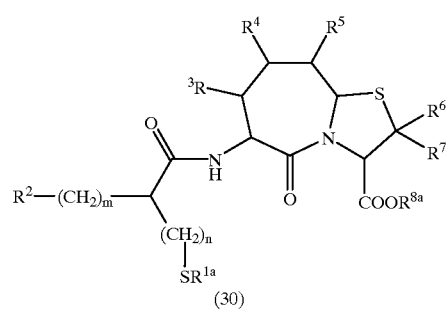
(30)
9th step | hydrolysis
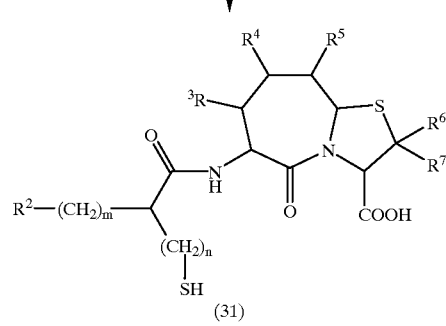
(31)
10th step | S-acylation
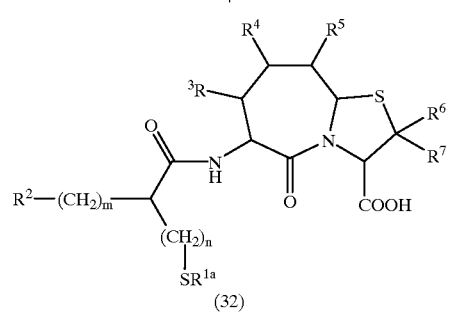
(32)

(in a series of formulae, $R^3$, $R^4$ and $R^5$ represent each independently a hydrogen atom, a lower alkyl group, a lower alkoxyl group, a lower alkylthio group, an aryl group which may have a substituent or a heteroaryl group which may have a substituent, or alternatively $R^3$, $R^4$ or $R^5$ may form a ring together with the carbon atom to which it is bonded, with the proviso that the case wherein all of $R^3$, $R^4$ and $R^5$ are hydrogen atoms is excepted; $R^6$ and $R^7$ each independently represent a hydrogen atom, lower alkyl, an aryl group which may be substituted or an aryalkyl group which may be substituted; $R^{1a}$ represents an acyl group; $R^{8a}$ represents a protecting group of a carboxyl group; $R^{12}$ represents a group forming an aldehyde equivalent together with the endocyclic nitrogen atom; Z represents an acyl group or a carbamate group; and m and n have the same meanings as those in the general formula (I)).

(1st step)

This step comprises acylating a pipecolic acid derivative (18) to give an N-acylpipecolic acid derivative (19). The compound (19) can be obtained by a conventional process. The compound (19) can be obtained, e.g., by reacting the compound (18) with an acid anhydride such as acetic anhydride at room temperature to 100° C., by reacting the compound (18) with an acid halide such as acetyl chloride and benzoyl chloride in the presence of a base such as pyridine and dimethylaminopyridine at 0° C. to room temperature, or, further, by so-called Schotten-Baumann reaction comprising reacting the compound (18) with an acid halide in the presence of a base, e.g., sodium hydroxide or sodium hydrogencarbonate.

(2nd step)

This step comprises esterifying the carboxylic acid of the N-acylpipecolic acid derivative (19) obtained in the 1st step to give an ester (20). The ester group is preferably a group which can be deprotected under such conditions that ordinary alkyl esters are not hydrolyzed during the deprotection of the ester, such as a t-butyl ester, a benzyl ester which may be substituted with a methoxy group or the like, and an alkylsilylethyl ester. When a t-butyl ester is prepared, it can be synthesized by reacting the compound (19) with isobutylene in an organic solvent such as dioxane and tetrahydrofuran in the presence of an acid catalyst such as sulfuric acid and p-toluenesulfonic acid or by reacting the compound (19) with t-butanol in the presence of a condensing agent such as N,N'-dicyclohexylcarbodiimide (DCC) and 1-(3-dimethylaminopropyl)-3-ethylcarbodiimide hydrochloride (DEC). When an ester such as a benzyl ester, a methoxybenzyl ester and an alkylsilylethyl ester is prepared, the compound (20) can be obtained by, conducting esterification with an esterifying agent such as a benzyl halide, a methoxybenzyl halide and an alkylsilylethyl halide in the presence of a base such as potassium carbonate, sodium carbonate and an alkylamine in an inert organic solvent such as tetrahydrofuran, dimethylformamide and dichloromethane.

(3rd step)

This step comprises electrolytically oxidizing the pipecolic acid derivative (20) obtained in the 2nd step to give a hemiacetal (21). The electrolytic oxidation may be conducted under various conditions. The hemiacetal (V) can be obtained, e.g., by electrolytically oxidizing the compound (20) with platinum, carbon, stainless steel, lead oxide or the like as an electrode by the use of, as a supporting electrolyte, an electrolyte enhancing the electric conductivity in an aqueous system or an organic solvent system, such as tetraalkylammonium perchlorates, e.g., tetraethylammonium perchlorate or tetramethylammonium perchlorate; alkali metal salts, e.g., sodium perchlorate or lithium perchlorate; tetraalkylammonium sulfonates, e.g., tetraethylammonium p-toluenesulfonate; tetraalkylammonium tetrafluoroborates; and tetraalkylammonium hexafluorophosphates, in a solvent such as a water/acetonitrile system, a water/alcohol system and a water/acetic acid system. The quantity of current passed is generally 2 F or more per mol of the compound (20) used. In particular, the case wherein platinum or carbon is used as the electrode and tetraethylammonium perchlorate, tetraethylammonium tetrafluoroborate or tetramethylammonium hexafluorophosphate is used as the supporting electrolyte gives a better result.

(4th step)

This step comprises reacting the hemiacetal (22) obtained in the 3rd step with a cysteine ester derivative (23) to give a thiazolidine derivative (24). In practice, the thiazolidine derivative (24) can be obtained by adding the cysteine ester derivative (23) to the reaction system after the completion of the 3rd step without isolation of the hemiacetal (22) to conduct treatment. When optically active L- or D-cysteine is used as the cystein to be used for this reaction, the absolute configuration of the carboxyl group at the 4-position of the thiazolidine ring of the compound (24) is R- or S-configuration.

(5th step)

This step comprises selectively deprotecting the protecting group of the carboxylic acid represented by R9 in the thiazolidine derivative (24) obtained in the 4th step to give a carboxylic acid derivative (25). The carboxylic acid derivative (25) can be obtained by a treating it with a de-t-butylating agent such as trifluoroacetic acid, hydrochloric acid and iodotrimethylsilane when the compound (24) is a t-butyl ester, or by a means which can usually deprotect only the corresponding ester protecting group, for example, catalytic hydrogenation, hydrochloric acid, 2,3-dichloro-5, 6-dicyano-1,4-benzoquinone (DDQ) or tetraalkylammonium fluoride when the compound (24) is an ester such as a benzyl ester, a methoxybenzyl ester and an alkylsilylethyl ester.

(6th step)

This step comprises cyclizing the thiazolidinecarboxylic acid derivative (25) obtained in the 5th step through condensation to give a thiazoloazepine derivative (26). The cyclization may be conducted with a conventional condensing agent. The cycled product (26) can be obtained, e.g., by reacting the compound (25) with 1-ethoxycarbonyl-2-ethoxy-1,2-dihydroquinoline (EEDQ), DCC, DEC or the like in a solvent such as ethanol, tetrahydrofuran and dichloromethane.

(7th step)

This step comprises deprotecting the N-acetyl group in the thiazoloazepine derivative (26) obtained in the 6th step to give an amino acid derivative (27). Although various ways of removing an N-acetyl group are known, the objective amino acid derivative (27) can be obtained, e.g., by heating it in an alcoholic solution of a dilute mineral acid such as hydrochloric acid and sulfuric acid, by treating it with an alcoholic solution of sodium hydroxide, potassium hydroxide or the like, or by reacting it with phosphorus pentachloride or oxalyl chloride in pyridine, followed by treatment with an alcohol.

(8th step)

This step comprises condensing the amino acid derivative (27) obtained in the 7th step with a carboxylic acid derivative represented by the general formula (29) or an active derivative thereof such as acid halide thereof to give an amide derivative (30). This condensation may be conducted by a conventional process, and an example thereof includes a condensation of the amino acid derivative (27) with the carboxylic acid derivative (29) in the presence of a condensing agent usually used, e.g., EEDQ, DCC, DEC or diethyl cyanophosphonate. Any organic solvent inert to the reaction can be used as the reaction solvent, and examples thereof include methylene chloride and tetrahydrofuran. When it is conducted via an acid halide such as acid chloride of the carboxylic acid derivative (29), the compound (30) can be obtained by reacting the carboxylic acid derivative (29) with a chlorinating agent usually used, e.g., thionyl chloride or oxalyl chloride in a suitable inert solvent to form an acid chloride thereof and reacting it with the amino acid derivative (27).

(9th step)

This step comprises hydrolyzing the α-acylthiocarboxylic amide derivative (30) obtained in the 8th step to give an α-mercaptocarboxylic amide derivative (31).

It can be hydrolyzed by a conventional hydrolysis, that is, in a dilute aqueous solution of an alkali such as sodium hydroxide and lithium hydroxide or in a dilute aqueous solution of a mineral acid.

(10th step)

This step comprises acylating the α-mercaptocarboxylic amide derivative (31) obtained in the 9th step to give an α-acylthiocarboxylic amide derivative (32).

The reaction may be conducted according to a conventional manner. The α-acylthiocarboxylic amide derivative (32) can be obtained, e.g., by reacting the a-mercaptocarboxylic amide derivative (31) with an acylating agent, such as an acid anhydride, e.g., acetic anhydride, and an acid halide, in a nonaqueous solvent such as acetonitrile, tetrahydrofuran and dichloromethane in the presence of a catalyst such as cobalt chloride, or by treating it in the presence of a base such as potassium hydrogencarbonate, sodium hydrogencarbonate and triethylamine in an aqueous solvent as well.

In particular, better results can be given with, as the acylating agent, an active ester prepared by reacting a carboxylic acid with carbodiimidazole.

In the above preparation process, the compounds represented by the general formula (27) are extremely important intermediates for the preparation of the compounds of the present invention.

Preparation process 2

(27)

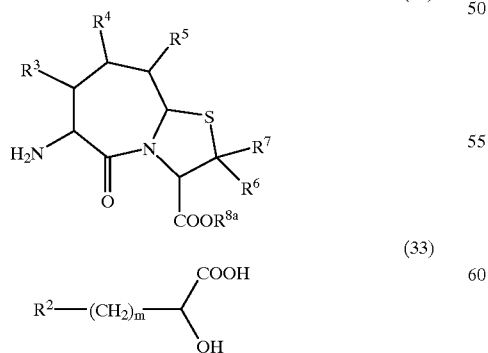

(33)

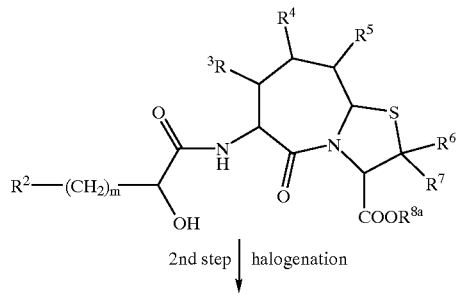

(34)

2nd step | halogenation

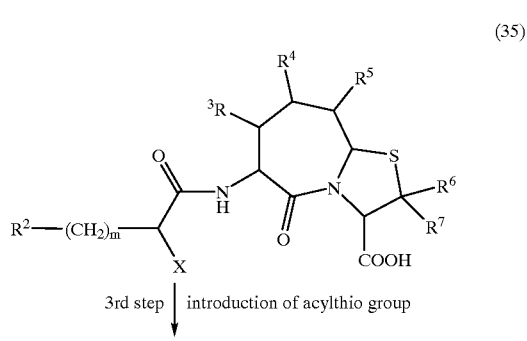

(35)

3rd step | introduction of acylthio group

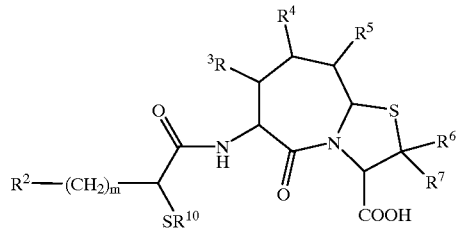

(36)

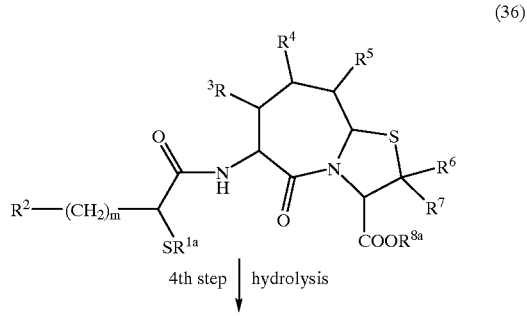

(36)

4th step | hydrolysis

-continued

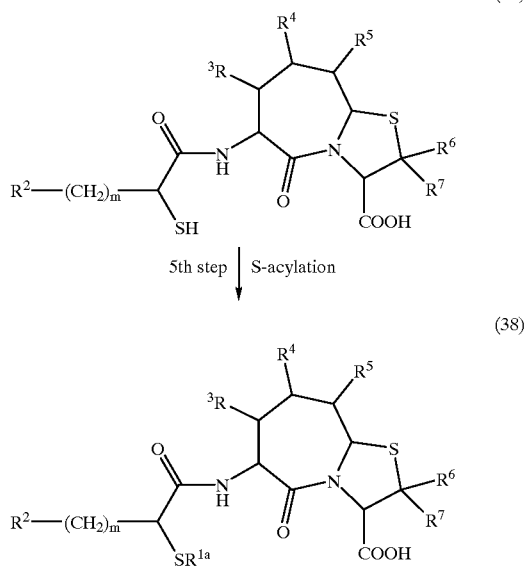

(in a series of formulae, $R^3$, $R^4$ and $R^5$ represent each independently a hydrogen atom, a lower alkyl group, a lower alkoxyl group, a lower alkylthio group, an aryl group which may have a substituent or a heteroaryl group which may have a substituent, or alternatively $R^3$, $R^4$ or $R^5$ may form a ring together with the carbon atom to which it is bonded, with the proviso that the case wherein all of $R^3$, $R^4$ and $R^5$ are hydrogen atoms are excepted;

$R^6$ and $R^7$ represent each independently a hydrogen atom, lower alkyl, an aryl group which may be substituted or an arylalkyl group which may be substituted; $R^{1a}$ represents an acyl group; $R^{8a}$ represents a protecting group of a carboxyl group; X represents a leaving group such as a halogen atom, a methanesulfonyloxy group or p-toluenesulfonyloxy group; and m and n have the same meanings as those in the general formula (I)).

(1st step)

This step comprises condensing the amino acid derivative (27) obtained in Preparation process 1 with a carboxylic acid derivative represented by the general formula (33) or an active derivative thereof such as an acid halide thereof to give an amide derivative (34). This condensation is conducted in the same manner as that of the 8th step of Preparation process 1 except that an α-hydroxycarboxylic acid derivative (33) is used instead of the carboxylic acid derivative (29).

(2nd step)

This step is one comprising halogenating the hydroxycarboxylic amide derivative (34) obtained in the 1st step to give an α-halocarboxylic amide derivative (35). There are known various processes for halogenating the compound (34) with the steric inversion of the hydroxyl group, for example, (i) a process comprising reacting it with dialkyl azodicarboxylate, triphenylphosphine and either zinc bromide or zinc iodide in an organic solvent such as tetrahydrofuran, (ii) a process comprising reacting it with an organophosphorus compound such as trialkylphosphine, triphenylphosphine and triphenyl phosphate and a halogen compound such as N-halosuccinimide and bromine/iodine in an organic solvent such as acetonitrile, dimethylformamide and dichloromethane in the presence or absence of a base such as pyridine and (iii) a process comprising reacting it with tosyl chloride, trifluoromethanesulfonic anhydride or the like in an inert solvent such as dichloromethane in the presence of a base such as pyridine and triethylamine to form a sulfonic acid ester, followed by reacting it with a halogenating agent such as a lithium halide. In particular, a process wherein triphenylphosphine and bromine are used under the condition (ii) is preferable.

(3rd step)

This step is one comprising introducing an acylthio group into the α-halocarboxylic amide derivative (35) obtained in the 2nd step to give an α-acylthiocarboxylic amide derivative (36).

The reaction may be conducted in a conventional manner. The α-acylthiocarboxylic amide derivative (36) can be obtained, e.g., by reacting the α-halocarboxylic amide derivative (35) with a thiocarboxylic acid salt such as potassium thioacetate and sodium thioacetate in a polar solvent such as acetonitrile and acetone, or by reacting the compound (35) with a thiocarboxylic acid such as thioacetic acid and thiobenzoic acid in the presence of a base such as potassium carbonate and cesium carbonate.

(4th step)

This step comprises hydrolyzing the α-acylthiocarboxylic amide derivative (36) obtained in the 3rd step to give an α-mercaptocarboxylic amide derivative (37). It can be hydrolyzed by a conventional hydrolysis, that is, in a dilute aqueous solution of an alkali such as sodium hydroxide and lithium hydroxide or in a dilute aqueous solution of a mineral acid.

(5th step)

This step is one comprising acylating the α-mercaptocarboxylic amide derivative (37) obtained in the 4th step to give an α-acylthiocarboxylic amide derivative (38).

The reaction is conducted according to a conventional manner. The α-acylthiocarboxylic amide derivative (38) can be obtained, e.g., by reacting the a-mercaptocarboxylic amide derivative (37) with an acylating agent such as an acid anhydride, e.g., acetic anhydride, and an acid halide, in a nonaqueous solvent such as acetonitrile, tetrahydrofuran and dichloromethane in the presence of a catalyst such as cobalt chloride, or by treating it in the presence of a base such as potassium hydrogencarbonate, sodium hydrogencarbonate and triethylamine in an aqueous solvent as well.

In particular, better results can be attained with, as the acylating agent, an active ester prepared by reacting a carboxylic acid with carbodiimidazole.

Preparation process 3

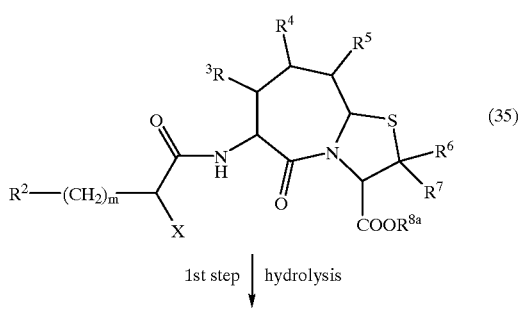

17
-continued

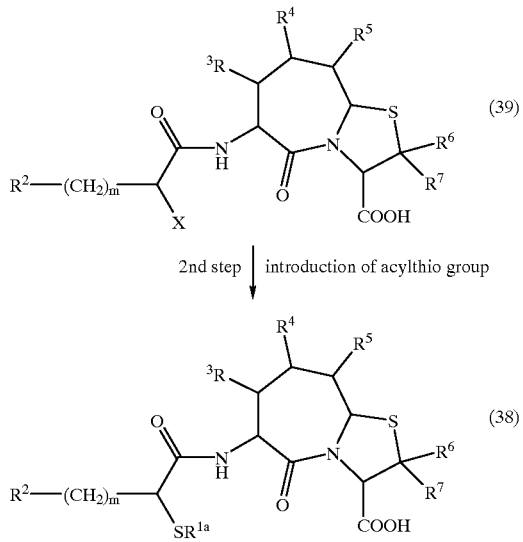

(in a series of formulae, $R^3$, $R^4$ and $R^5$ represent each independently a hydrogen atom, a lower alkyl group, a lower alkoxyl group, a lower alkylthio group, an aryl group which may have a substituent or a heteroaryl group which may have a substituent, or alternatively $R^3$, $R^4$ or $R^5$ may form a ring together with the carbon atom to which it is bonded, with the proviso that the case wherein all of $R^3$, $R^4$ and $R^5$ are hydrogen atoms are excepted;

$R^6$ and $R^7$ represent each independently a hydrogen atom, lower alkyl, an aryl group which may be substituted or an arylalkyl group which may be substituted; $R^{1a}$ represents an acyl group; $R^{8a}$ represents a protecting group of a carboxyl group; X represents a leaving group such as a halogen atom, a methanesulfonyloxy group and a p-toluenesulfonyloxy group; and m and n have the same meanings as those in the general formula (I)).

(1st step)

This step comprises hydrolyzing the ester group of the halide (35) obtained in Preparation process 2 to give a carboxylic acid derivative (39). It can be hydrolyzed by a conventional hydrolysis, that is, in a dilute aqueous solution of an alkali such as sodium hydroxide and lithium hydroxide or in a dilute aqueous solution of a mineral acid.

(2nd step)

This step comprises introducing an acylthio group into the α-halocarboxylic amide derivative (39) obtained in the 1st step to give an α-acylthiocarboxylic amide derivative (38). The reaction may be conducted in a conventional manner. The α-acylthiocarboxylic amide derivative (38) can be obtained, e.g., by reacting the α-halocarboxylic amide derivative (38) with a thiocarboxylic acid salt such as potassium thioacetate and sodium thioacetate in a polar solvent such as acetonitrile, dimethyl sulfoxide and acetone, or by reacting the derivative (38) with a thiocarboxylic acid such as thioacetic acid and thiobenzoic acid in the presence of a base such as potassium carbonate and cesium carbonate.

18
Preparation process 4

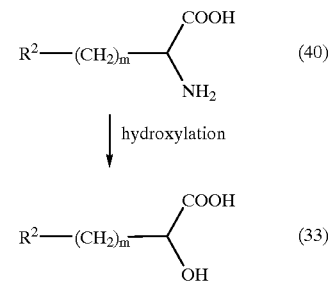

(in a series of formulae, $R^2$ and m have the meanings as described above).

This step comprises replacing the amino group of a natural or non-natural amino acid (40) by a hydroxyl group to give an α-hydroxycarboxylic acid (33). The replacement by a hydroxyl group is conducted either by reacting the amino acid (40) with a nitriting agent such as sodium nitrite in dilute sulfuric acid or by reacting the amino acid (40) with sodium nitrite in acetic acid to form an acetate, followed by conducting hydrolysis.

When all of R4 and R5 are hydrogen atoms with respect to preferable compounds (I') among compounds of the present invention, it has already been known a process wherein the compound is obtained by subjecting the compound (II) and the compound (i), (ro) or (ha) to amidation.

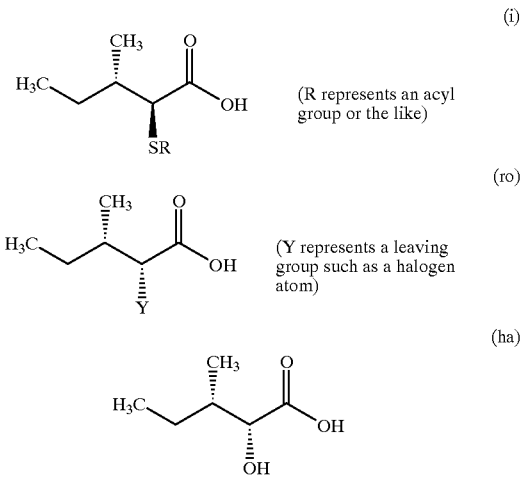

However, it is difficult to say that the above process is industrially advantageous, because all of the above compounds (i), (ro) and (ha) are expensive and D-allo-isoleucine, of which the mass production requires much labor, is employed as the starting material. The processes which will be described below are industrially advantageous processes by which the compound (I') can be prepared in a high yield with advantage in operation.

Preparation process 5

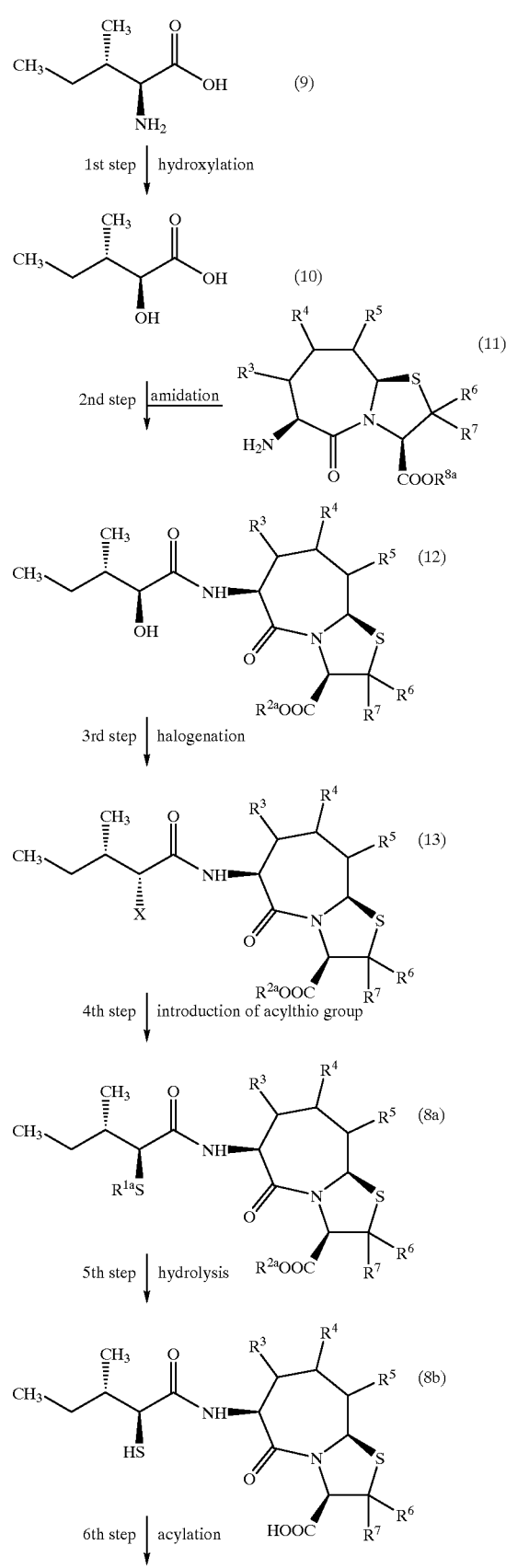
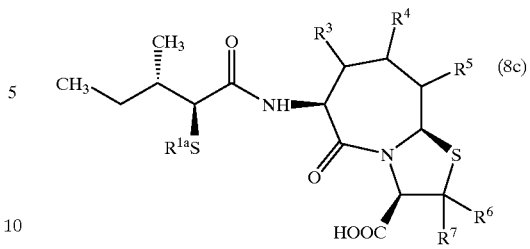

(1st step)

This step comprises hydroxylating the amino group of L-isoleucine (9) in a conventional manner to give an α-hydroxycarboxylic acid (10). Although the hydroxylation may be conducted by a method usually used, it is preferably conducted either by reacting L-isoleucine (9) with a nitriting agent such as sodium nitrite in dilute sulfuric acid or by reacting L-isoleucine (9) with sodium nitrite in acetic acid to form an acetate, followed by conducting hydrolysis.

(2nd step)

This step comprises condensing the α-hydroxycarboxylic acid (10) obtained in the 1st step with an amine derivative (11) in a conventional manner to give a hydroxycarboxylic amide derivative (12).

The reaction may be conducted by a method usually used. The amide derivative (12) can be obtained, e.g., by reacting the α-hydroxycarboxylic acid (10) with the amine derivative (11) in the presence of a condensing agent usually used, for example, EEDQ, DCC, DEC or diethyl cyanophophonate, in an inert solvent such as methylene chloride and tetrahydrofuran.

(3rd step)

This step comprises halogenating the hydroxycarboxylic amide derivative (12) in a conventional manner to give an α-halocarboxylic amide derivative (13).

Every process usually used may be employed, as long as it is a process which attains halogenation accompanied with steric inversion. Examples of such processes include (i) a process comprising reacting it with dialkyl azodicarboxylate, triphenylphosphine and either zinc bromide or zinc iodide in an organic solvent such as tetrahydrofuran (ii) a process comprising reacting it with an organophosphorus compound such as a trialkylphosphine, triphenylphosphine and triphenyl phosphate and a halogen compound such as N-halosuccinimide and bromine/iodine in an organic solvent such as acetonitrile, dimethylformamide and dichloromethane in the presence or absence of a base such as pyridine and (iii) a process comprising reacting it with tosyl chloride, trifluoromethanesulfonic anhydride or the like in the presence of a base such as pyridine and triethylamine in an inert solvent such as dichloromethane to form a sulfonic acid ester, followed by reacting it with a halogenating agent such as lithium halide. Particularly preferably is a process comprising reacting it with an organophosphorus compound such as a trialkylphosphine, triphenylphosphine and triphenyl phosphite and a halogen compound such as N-halosuccinimide and bromine/iodine in an organic solvent such as acetonitrile, dimethylformamide and dichloromethane in the presence or absence of a base such as pyridine. The process comprising using triphenylphosphine and bromine as reagents is particularly preferable.

(4th step)

This step comprises introducing an acylthio group into the α-halocarboxylic amide derivative (13) obtained in the 3rd step to give an α-acylthiocarboxylic amide derivative (8a).

The reaction may be conducted in a conventional manner. The α-acylthiocarboxylic amide derivative (8a) can be obtained, e.g., by reacting the α-halocarboxylic amide derivative (13) with a thiocarboxylic acid salt such as potassium thioacetate and sodium thioacetate in a polar solvent such as acetonitrile and acetone or by reacting the derivative (13) with a thiocarboxylic acid such as thioacetic acid and thiobenzoic acid in the presence of a base such as potassium carbonate and cesium carbonate.

(5th step)

This step is conducted when $R^1$ and $R^8$ are hydrogen atoms or when $R^1$ is an acyl group and $R^8$ is a hydrogen atom. In other words, it is a step wherein a (2S, 3S)-3-methyl-2-thiopentanoic acid derivative (8b) is obtained by hydrolyzing the α-acylthiocarboxylic amide derivative (8a) obtained in the 4th step in a conventional manner.

It can be hydrolyzed by a conventional hydrolysis, that is, in a dilute aqueous solution of an alkali such as sodium hydroxide and lithium hydroxide or in a dilute aqueous solution of a mineral acid. When the desired compound is one wherein $R^1$ is an acyl group, the following 6th step is conducted with the use of the obtained (2S, 3S)-3-methyl-2-thiopentanoic acid derivative (8b).

(6th step)

This step is conducted when the objective compound is one wherein $R^1$ is an acyl group. In other words, it is a step comprising acylating the (2S, 3S)-3-methyl-2-thiopentanoic acid derivative (8b) obtained in the 5th step in a conventional manner to give an α-acylthiocarboxylic amide derivative (8c).

The reaction may be conducted by a method usually used. The α-acylthiocarboxylic amide derivative (8c) can be obtained, e.g., by reacting the α-mercaptocarboxylic amide derivative (8b) with an acylating agent such as an acid anhydride, e.g., acetic anhydride, and an acid halide in a nonaqueous solvent such as acetonitrile, tetrahydrofuran and dichloromethane or by treating it in the presence of a base such as potassium hydrogencarbonate, sodium hydrogencarbonate and triethylamine, or cobalt chloride in an aqueous solvent as well.

The objective compound can be also obtained by the process which will be described below after obtaining the α-halohydroxycarboxylic amide derivative (13) by hydroxylating L-isoleucine and condensing it with the amine derivative (11) according to the Preparation process 5.

Preparation process 6

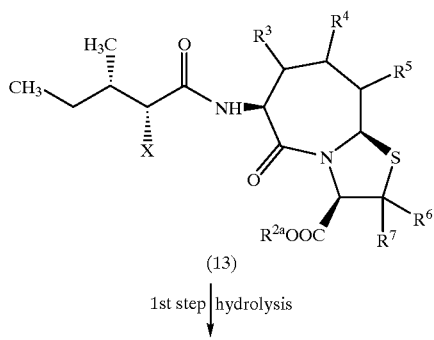

(13)

1st step | hydrolysis

-continued

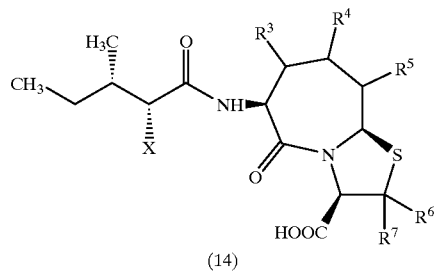

(14)

2nd step | introduction of acylthio group

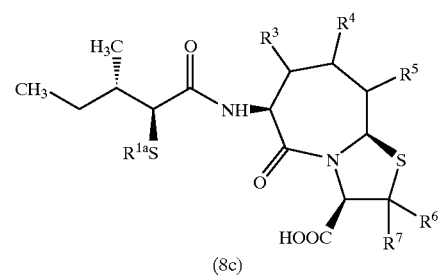

(8c)

(1st step)

This step comprises hydrolyzing the α-halocarboxylic amide derivative (13) obtained in the 3rd step of Preparation process 5 in a conventional manner to give a carboxylic acid (14).

It can be hydrolyzed by a conventional hydrolysis, that is, in a dilute aqueous solution of an alkali such as sodium hydroxide and lithium hydroxide or in a dilute aqueous solution of a mineral acid.

(2nd step)

This step comprises introducing an acylthio group into the α-halocarboxylic amide derivative (14) obtained in the 1st step to give an α-acylthiocarboxylic amide derivative (8c). The reaction is conducted in a conventional manner. The α-acylthiocarboxylic amide derivative (8c) can be obtained, e.g., by reacting the α-halocarboxylic amide derivative (14) with a thiocarboxylic acid salt such as potassium thioacetate and sodium thioacetate in a polar solvent such as acetonitrile, dimethyl sulfoxide and acetone or by reacting the derivative (14) with a thiocarboxylic acid such as thioacetic acid and thiobenzoic acid in the presence of a base such as potassium carbonate and cesium carbonate.

U.S. Pat. No. 4,415,496 and U.S. Pat. No. 4,617,301 disclose, among amines represented by the general formula (II), amines (II''') wherein all of R3, R4 and R5 are hydrogen atoms. As processes for obtaining this amines (II'''), there have been known, for example, a process described in U.S. Pat. No. 4415496 which uses (S)-2-amino-6-hydroxyhexanoic acid as the starting material and a process described in U.S. Pat. No. 4,617,301 and U.S. Pat. No. 5,118,810 which uses ε-N-BOC-L-lysine as the starting material, up to now. However, it is difficult to say that the operations are advantageous, since the starting materials are difficultly available, and they require many steps, and an ion exchange resin and much Raney nickel, in all of them. The production processes which will be described below are those which make it possible to prepare not only the amines (II''') whose industrial production was remarkably restricted in operational and industrial respects but also the amines wherein any one or two or more of R3, R4 and R5 is(are) a group(s) other than a hydrogen atom which could not easily be prepared by the preparation processes disclosed as the preparation process of the amines (II'''), at a low cost in a high yeild with advantage in respect of operation.

Preparation process A

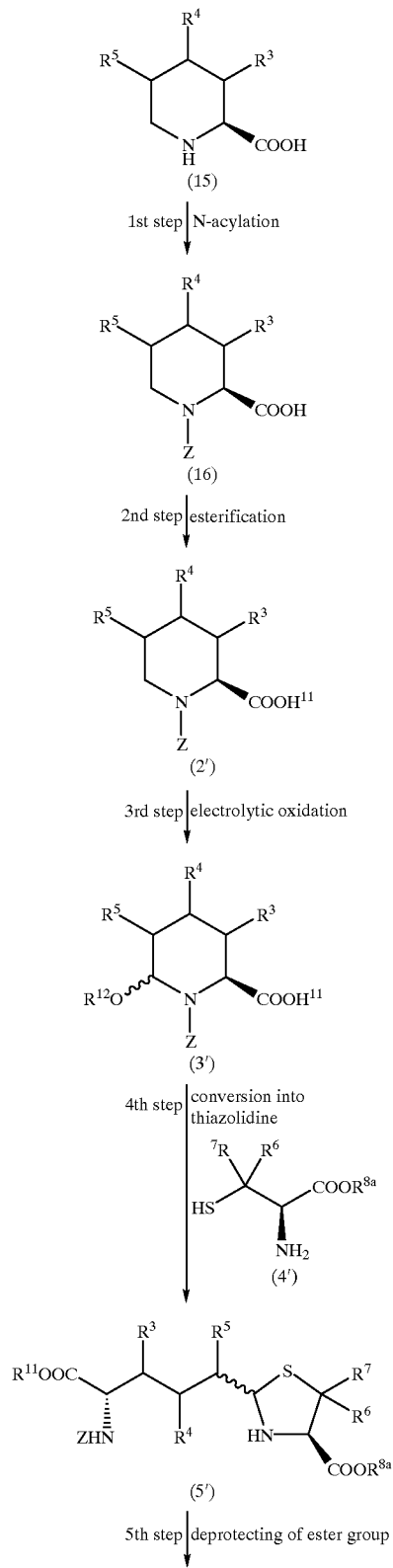

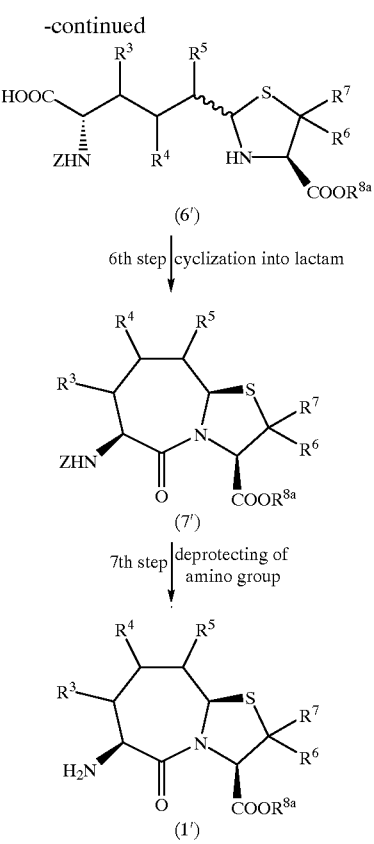

(in a series of formulae, $R^3$, $R^4$ and $R^5$ represent each independently a hydrogen atom, a lower alkyl group, a lower alkoxyl group, a lower alkylthio group, an aryl group which may have a substituent or a heteroaryl group which may have a substituent, or alternatively $R^3$, $R^4$ or $R^5$ may form a ring together with the carbon atom to which it is bonded, with the proviso that the case wherein all of $R^3$, $R^4$ and $R^5$ are hydrogen atoms are excepted;

$R^6$ and $R^7$ represent each independently a hydrogen atom, a lower alkyl group, an ary group which may be substituted or an arylalkyl group which may be substituted; $R^{2a}$ represents a protecting group of a carboxyl group; $R^{12}$ represents a group forming an aldehyde equivalent together with the endocyclic nitrogen atom; and Z represents an acyl group or a carbamate group).

(1st step)

This step comprises acylating an optically active (2S)-pipecolic acid derivative (15) to give an N-acylpipecolic acid derivative (16). The compound (16) can be obtained by a conventional acylation. The compound (16) can be obtained, e.g., by reacting the compound (15) with an acid anhydride such as acetic anhydride at room temperature to 100° C., or by reacting the compound (15) with an acid halide such as acetyl chloride and benzoyl chloride in the presence of a base such as pyridine and dimethylaminopyridine at 0° C. to room temperature, or, further, by so-called Schotten-Baumann reaction comprising reacting the compound (15) with an acid anhydride or an acid halide in the presence of a base, e.g., sodium hydroxide, sodium carbonate or sodium hydrogen-carbonate.

(2nd step)

This step comprises esterifying the carboxylic acid of the N-acylpipecolic acid derivative (16) obtained in the 1st step to give an ester (2'). The ester group is preferably a group which can be deprotected under such conditions that ordinary alkyl esters are not hydrolyzed during the deprotection of the ester, such as a t-butyl ester, a benzyl ester which may be substituted with a methoxy group or the like, and an alkylsilylethyl ester. When a t-butyl ester is prepared, it can be synthesized by reacting the compound (16) with isobutylene in an ethereal solvent such as dioxane and tetrahydrofuran or an organic solvent such as dichloromethane in the presence of an acid catalyst such as sulfuric acid and p-toluenesulfonic acid or by-reacting the compound (16) with t-butanol in the presence of a condensing agent such as dicyclohexylazodicarboxylate (DCC) and 1-(3-dimethylaminopropyl)-3-ethylcarbodiimide. (DEC). While, when an ester such as a benzyl ester, a methoxybenzyl ester and an alkylsilylethyl ester is prepared, the compound (2') can be obtained by conducting esterification with an esterifying agent such as a benzyl halide, a methoxybenzyl halide and an alkylsilylethyl halide in the presence of a base such as potassium carbonate, sodium carbonate and an alkylamine in an inert organic solvent such as tetrahydrofuran, dimethylformamide and dichloromethane.

(3rd step)

This step comprises electrolytically oxidizing the pipecolic acid derivative (2') obtained in the 2nd step to give a hemiacetal (3').

The electrolytic oxidation may be conducted under various conditions. The hemiacetal (3') can be obtained, e.g., by electrolytically oxidizing the compound (2') with platinum, carbon, stainless steel, lead oxide or the like as an electrode by the use of, as a supporting electrolyte, an electrolyte enhancing the electric conductivity in an aqueous system or an organic solvent system, such as tetraalkylammonium perchlorates, e.g., tetraethylammonium perchlorate or tetramethylammonium perchlorate; alkali metal salts, e.g., sodium perchlorate or lithium perchlorate; tetraalkylammonium sulfonates, e.g., tetraethylammonium p-toluenesulfonate; tetraalkylammonium tetrafluoroborates; and tetraalkylammonium hexafluorophosphates, in a solvent such as a water/acetonitrile system, a water/alcohol system and a water/acetic acid system. The quantity of current passed is generally used 2 F per mol or more, based on the compound (2') used. In particular, the case wherein platinum or carbon is used as the electrode and tetraethylammonium perchlorate, tetraethylammonium tetrafluoroborate, tetramethylammonium hexafluorophosphate or tetraethylammonium p-toluenesulfonate is used as the supporting electrolyte gives a better result.

(4th step)

This step comprises reacting the hemiacetal (3) obtained In the 3rd step with an L-cysteine ester derivative (4) to give a thiazolidine derivative (5). The thiazolidine derivative (5) can be obtained by adding the L-cysteine ester derivative (4) to the reaction system after the completion of the 3rd step without isolation of the hemiacetal (3) to conduct treatment.

(5th step)

This step comprises selectively deprotecting the protecting group of the carboxylic acid represented by R11 in the thiazolidine derivative (5') obtained in the 4th step to give a carboxylic acid derivative (6'). The carboxylic acid derivative (6') can be obtained by treating it with a de-t-butylating agent such as trifluoroacetic acid, hydrochloric acid and iodotrimethylsilane when the compound (5') is a t-butyl ester, or by means which can usually deprotect only the corresponding ester protecting group, for example, catalytic hydrogenation, hydrochloric acid, 2,3-dichloro-5,6-dicyano-1,4-benzoquinone (DDQ) or tetraalkylammonium fluoride when the compound (5') is an ester such as a benzyl ester, a methoxybenzyl ester and an alkylsilylethyl ester.

(6th step)

This step comprises cyclizing the thiazolidinecarboxylic acid derivative (6') obtained in the 5th step through condensation to give an amino acid derivative (7'). The cyclization may be conducted with a conventional condensing agent. The amino acid derivative (7') as a cyclic product can be obtained, e.g., by reacting the compound (6') with 2-ethoxy-1-ethoxy-1,2-dihydroquinoline (EEDQ), DCC, DEC or the like in a solvent such as ethanol, tetrahydrofuran and dichloromethane.

(7th step)

This step comprises deprotecting the N-acetyl group in the amino acid derivative (7') obtained in the 6th step to give an amino acid derivative (1'). Although various removements of an N-acetyl group are known, the objective amino acid derivative can be obtained, e.g., by heating it in an alcoholic solution of a dilute mineral acid such as hydrochloric acid and sulfuric acid, by treating it with an alcoholic solution of sodium hydroxide. potassium hydroxide or the like, or by reacting it with phosphorus pentachloride or oxalyl chloride in pyridine, followed by the treatment with an alcohol.

Preparation process B

The steps of from the 1st step to the 2nd step of Preparation process A can also be conducted by the following process:

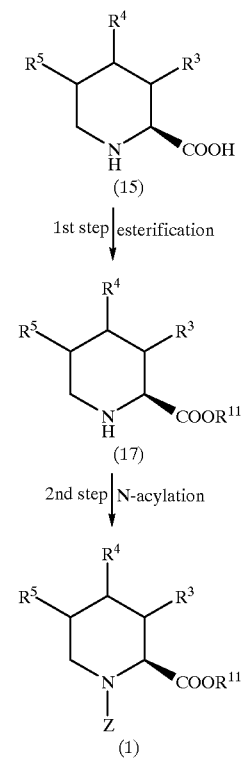

(in a series of formulae, $R^3$, $R^4$ and $R^5$ represent each independently a hydrogen atom, a lower alkyl group, a lower alkoxyl group, a lower alkylthio group, an aryl group which may have a substituent or a heteroaryl group which may have a substituent, or alternatively $R^3$, $R^4$ or $R^5$ may form a ring together with the carbon atom to which it is bonded, with the proviso that the case wherein all of $R^3$, $R^4$ and $R^5$ are hydrogen atoms are excepted;

$R^{11}$ represents a protecting group of a carboxyl group; and Z represents an acyl group or a carbamate group).

(1st step)

This step comprises t-butyl-esterifying an optically active (2S)-pipecolic acid derivative (15) to give an ester (17). The ester (15) can be obtained in the same manner as that described in the 2nd step of Preparation process A, that is, by reacting the compound (2) with isobutylene in an organic solvent such as dioxane and tetrahydrofuran in the presence of an acid catalyst such as sulfuric acid and p-toluenesulfonic acid or by reacting the compound (2) with t-butanol in the presence of a condensing agent such as dicyclohexyl azodicarboxylate (DCC) and 1-(3-dimethylaminopropyl)-3-ethylcarbodiimide (DEC).

(2nd step)

This step comprises acylating the nitrogen atom in the ester (17) obtained in the 1st step to give an acylpipecolic acid derivative (2). The compound (2) can be obtained in the same manner as that described in the 1st step of Preparation process A. That is, the compound (2) can be obtained by reacting the compound (17) with an acid anhydride such as acetic anhydride at room temperature to 100° C., or by reacting the compound (15) with an acid halide such as acetyl chloride and benzoyl chloride in the presence of a base such as pyridine and dimethylaminopyridine at 0° C. to room temperature, or, further, by so-called Schotten-Baumann reaction comprising reacting the compound (15) with an acid halide in the presence of a base, e.g., sodium hydroxide or sodium hydrogencarbonate.

Preparation process C

When R5 is a branched alkyl group, it can also be prepared by the following process:

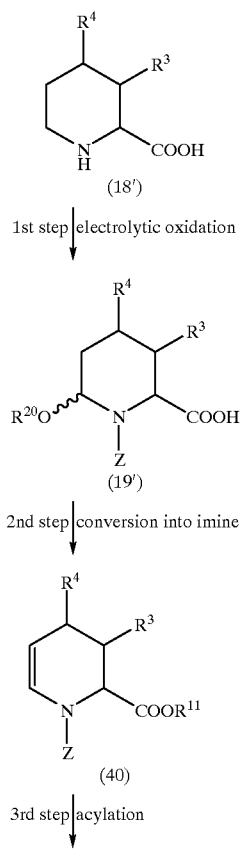

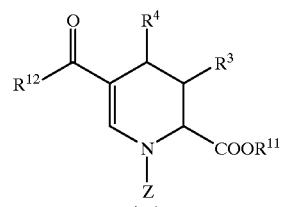

4th step | reduction

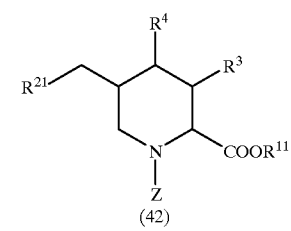

(1st step)

This step comprises electrolytically oxidizing the pipecolic acid derivative (18') obtained in a conventional manner or a conventional manner to give a hemiacetal (19'). The electrolytic oxidation may be conducted under various conditions. The hemiacetal (19') can be obtained, e.g., by electrolytically oxidizing the compound (18') with platinum, carbon, stainless steel, lead oxide or the like as an electrode by the use of an alkali metal salt such as tetraethylammonium perchlorate and tetramethylammonium perchlorate, a tetraalkylammonium hexafluorophosphate such as tetraethylammonium p-toluenesulfonate, or the like as a supporting electrolyte in a solvent such as a water/alcohol system and a water/acetic acid system. The quantity of current passed is generally used 2 F or more per mol of the compound (18') used. In particular, the case wherein platinum or carbon is used as the electrode and tetraethylammonium tetrafluoroborate or tetramethylammonium hexafluorophosphate is used as the supporting electrolyte gives a better result.

(2nd step)

This step comprises conducting 1,2-elimination of the hemiacetal (19') obtained in the 1st step to give an imino derivative (40). The compound (40) can be obtained in a conventional elimination such as an acid catalyst and a thermal reaction.

(3rd step)

This step comprises acylating the imino derivative (40) obtaineded in the 2nd step to give a ketone (41). Generally, various acyl groups can be introduced thereinto by utilizing electrophilic substitution reaction against the imino group. The ketone (41) can be obtained, e.g., by the Volsmeier process which is conducted in an inert solvent such as dichloromethane, chloroform and dimethyl formamide by the use of phosphorus oxychloride, thionyl chloride or the like, by a formylation process such as the Gattermann-Koch process or by the Friedel-Crafts process using aluminum chloride, titanium tetrachloride or the like.

(4th step)

This step comprises reducing the carbonyl group of the ketone (41) obtaineded in the 3rd step to give a methylene compound (42). The agar of the ketone may be conducted in a conventional manner. The methylene compound (42) can be obtained, e.g., by catalytic hydrogenation, the Wolff-Kishner reduction using hydrazine or a reduction using a hydrosilane such as trichlorosilane and triethylsilane.

Preparation process D

When R5 is a branched alkyl group, it can also be prepared by the following process:

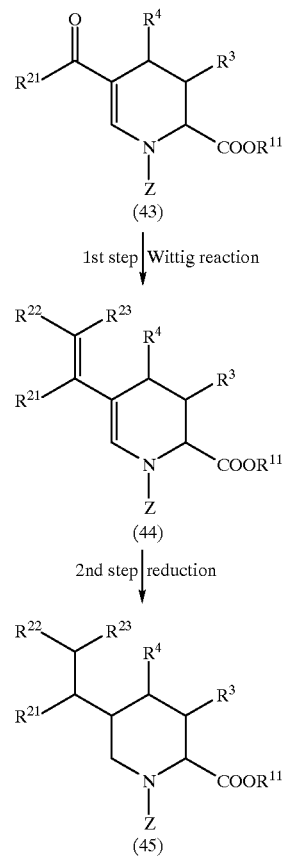

(1st step)

This step comprises converting the carbonyl of the acyl compound (43) obtained in the 3rd step of Preparation process C into an olefin to give an olefin compound (44). The olefin compound (44) can be obtained by a conversion reaction of carbonyl to olefin, e.g., the Wittig reaction using alkylidinephosphorane and a strong base such as sodium amide and n-butyllithium, or the Horner process using a phosphonic acid ester.

(2nd step)

This step comprises reducing the double bond of the olefin compound (44) obtained in the 1st step to give a saturated derivative (45). The saturated derivative (45) can be obtained by a conventional reaction for reducing a double bond, for example, catalytic hydrogenation.

As described above, the compounds of the present invention can be prepared also industrially advantageously, and are excellent compounds also in this respect.

Pharmacological Experimental Examples will now be described to illustrate the usefulness of the compounds of the present invention in detail.

PHARMACOLOGICAL EXPERIMENTAL
EXAMPLE 1

Determination of NEP Inhibiting activities of Medicaments with Rat Kidney Cortex 1. Experimental method NEP activity was determined with the membrane fraction prepared from the kidney cortex of rat according to the process of Booth and Kenny (A Rapid Metod for the Purificaton of Microvilli from Rabbit Kidney., Andrew G. Booth and A. John Kenny, Biochem J., 1974, 142, 575–581).

The NEP activity was determined according to the process of Orlowsky and Wilk (Purification and Specificity of a Membrane-Bound Metalloendpeptidase from Bovine Pituitaries., Marian Orlowsky and Shrwin Wilk, Biochemistry, 1981, 20, 4942–4950.) by the following method.

Benzoyl-glycyl-arginyl-arginyl-2-naphthylamide (Benzoyl-Gly-Arg-Arg-2-napththylamide (Nova Biochem, Switzerland)) was used as substrate. The naphthylamine liberated in the presence of the NEP enzyme sample and excess of leucine aminopeptidase (Sigma Chemical Co., U.S.A.) was color-developed with first garnet (Sigma Chemical Co., U.S.A.) and the absorbance at a wavelength of 540 nm was determined.

The NEP inhibiting activity was determined by adding the test compound to the above experiment system in final concentrations of 1, 3, 10, 30, 100, 300 and 1000 nM to form an inhibition curve and determining the concentration at which 50% of the activity was inhibited as IC50. [4S-(4α, 7α(R*), 12bβ]]-7-[(1-oxo-2(S)-thio-3-phenylpropyl) amino]-1,2,3,4,6,7,8,12b-octahydro-6-oxopyrido[2,1-a] [2] benzazepine-4-carboxylic acid (which is a compound disclosed in Japanese Patent Publication-A No. 4-2528382) was used as the control compound.

2. Experimental results

The results of the above experiment are given in Table 1 which will be described below.

PHARMACOLOGICAL EXPERIMENTAL
EXAMPLE 2

Determination of ACE Inhibiting Activities of Medicaments with Rat Lung

1. Experimental method

ACE inhibiting activity was examined with the membrane fraction prepared from the lung of rat according to the method of Wu-Wong et al. (Characterization of Endthelin Converting Enzyme in Rat Lung, Junshyum R. Wu-Wong, Gerald P. Budzik, Edward M. Devine and Terry J. Opgenorth, Biochem. Biophys. Res. Commun., 1990, 171, 1291–1296.).

The ACE activity was determined by a modification (wherein the pH of the borate buffer was changed to 8.3) of the Cushman-Cheung method (Spectrophotometric Assay and Properties of the Angiotensin-Converting Enzyme of Rabbit Lung., Cushman D. W. and Cheung H. S., 1971, 20, 1637–1648).

The hippurate liberated from Hippuryl-histidyl-leucine (Hippuryl-His-Leu (Peptidelnstitute Inc., Japan)) in the presence of ACE was extracted with ethyl acetate and the absorbance at a wavelength of 228 nm was determined.

The ACE inhibiting activity was determined by adding the test compound to the above experiment system in final concentrations of 1, 3, 10, 30, 100, 300 and 1000 nM to form an inhibition curve and determining the concentration at which 50% of the activity was inhibited as IC50. [4S-[4α, 7α(R*), 12bβ])-7-[(1-oxo-2(S)-thio-3-phenylpropyl) amino]-1,2,3,4,6,7,8,12b-octahydro-6-oxopyrido[2,1-a] [2]benzazepine-4-carboxylic acid (which is a compound disclosed in Japanese Patent Publication-A No. 4-282382) was used as the control compound.

2. Experimental results

The results of the experiment conducted by the above experimental method are given in Table 1.

| NEP- and ACE-inhibiting activities of Example compounds and comparative compound | | |
|---|---|---|
| | NEP inhibiting activity IC$_{50}$ (nM) | ACE inhibiting activity IC$_{50}$ (nM) |
| Ex. 3 | 4.3 | 2.5 |
| Ex. 11 | 6.7 | 2.2 |
| Ex. 24 | 1.5 | 2.5 |
| Ex. 9 | 13 | 5.1 |
| Ex. 10 | 12 | 4.3 |
| Comparative compound*[1] | 27 | 9 | note)
*[1]comparative compound: [4S-[4α, 7α(R*), 12bβ]]-7-[(1-oxo-2(S)-thio-3-phenylpropyl)amino]-1,2,3,4,6,7,8,12b-octahydro-6-oxopyrido[2,1-a][2]benzazepine-4-carboxylic acid (designation of the compound MDL-100, 173)

Example

Examples will now be described to further facilitate the understanding of the present invention. However, it is needless to say that the present invention is not limited to them. Prior to Examples, the Production Examples of the compounds which are used as the starting compounds for the compounds of the present invention will be illustrated as Synthesis Examples.

Synthesis Example 1

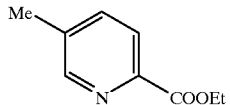

200 ml of ethanol and 100 ml (1.88 mol) of concentrated sulfuric acid were added to 55.5 g of 5-methylpyridine-2-carbonitrile to form a homogeneous solution, followed by heating under reflux for 2 days. The reaction liquid was gradually poured into a saturated aqueous solution of sodium hydrogencarbonate under cooling with ice to neutralize the sulfuric acid, followed by extraction with dichloromethane. The organic layer was washed with a saturated aqueous solution of common salt and dried over anhydrous sodium sulfate. After filtration, the filtrate was concentrated in a reduced pressure to give 78.1 g of a brown oil of the title compound as the crude product.

1H-NMR (400 MHz, CDCl$_3$)δ; 8.57 (1H, m), 8.03 (1H, dt, J=8.0, 0.5 Hz), 7.63 (1H, ddd, J=1.0, 2.5, 8.0 Hz), 4.47 (2H, q, J=7.0 Hz), 2.42 (3H, s), 1.44 (3H, t, J=7.0 Hz).

Synthesis Example 2

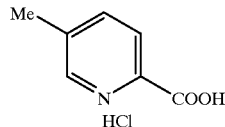

78.1 g of the crude product of the ethyl 5-methylpyridine-2-carboxylate obtained in Synthesis Example 1 was dissolved in 200 ml of 6N-hydrochloric acid, followed by heating under reflux for 16 hours. The reaction solution was concentrated in a reduced pressure. Then, acetonitrile was added to the residue, and the white crystal thus precipitated was recovered by filtration, washed with acetonitrile and dried at 90° C. to give 26.3 g of the title compound. Yield 37%.

1H-NMR (400 MHz, CDCl$_3$)δ; 8.51 (1H, m), 8.37 (1H, m), 8.21 (1H, d, J=8.0 Hz), 2.42 (3H, s).

Synthesis Example 3

(2S*, 5S*)-2-Carboxy-5-methylpiperidinium chloride and (2S*, 5R*)-2-carboxy-5-methylpiperidinium chloride

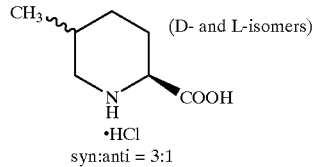

26.3 g (151 mmol) of the 2-carboxy-5-methylpyridinium chloride obtained in Synthesis Example 2 was dissolved in 300 ml of ethanol-water (1:1). Then, 2 g of platinum oxide was added thereto, followed by hydrogenation at 50° C. and at 16 atm overnight. After removing the catalyst by filtration, the filtrate was concentrated in a reduced pressure, and the thus-obtained white crystal was dried at 90° C. to give 27.0 g of the title compound as a mixture (a diastereomeric ratio 3:1). Yield 99%.

1H-NMR (400 MHz, D$_2$O)δ; 4.06 (¾H, t, J=5.0 Hz), 3.71 (¼H, m), 3.24 (¼H, ddd, J=1.5, 4.0, 13.0 Hz), 3.10 (¾H, dd, J=4.5, 13.0 Hz), 2.82 (¾H, dd, J=10.0, 13.0 Hz), 2.53 (¼H, t, J=13.0 Hz), 2.22–2.04 (1H, m), 1.90–1.52 (2H, m), 1.22–1.04 (1H, m), 0.82 (3×¾H, d,J=7.0 Hz), 0.81 (3×¼H, d, J=7.0 Hz).

Synthesis Example 4

(2S*, 5S*)-N-Acetyl-5-methylpiperidine-2-carboxylic acid

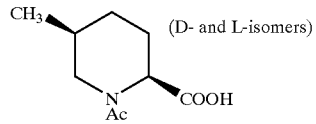

27.0 g (150 mmol) of the mixture of (2S*, 5S*)-2-carboxy-5-methylpiperidinium chloride and (2S*, 5R*)-2-carboxy-5-methylpiperidinium chloride obtained in Synthesis Example 3 was suspended in 700 ml of dichloromethane. Then, 21 ml (150 mmol) of triethylamine was added thereto, follwed by stirring at room temperature for 2 hours. A white crystal was recovered by filtration, washed with dichloromethane and then dried at 50° C. to give 15.9 g of (2S*, 5S*)-5-methylpiperidine-2-carboxylic acid. Yield 74%.

15.9 g (111 mmol) of the (2S*, 5S*)-5-methylpiperidine-2-carboxylic acid described above was dissolved in 220 ml of a dichloromethane/water (1:1). 93.3 g (1.11 mol) of sodium hydrogencarbonate and 21.0 ml (222 mmol) of acetic anhydride were added thereto in this order at room temperature, followed by stirring for 3 days. The reaction solution was poured into 6N-hydrochloric acid under cooling with ice, and the extraction with chloroform was conducted. Then, the organic layer was dried over anhydrous sodium sulfate. After filtration, the filtrate was concentrated in a reduced pressure to give 20.1 g of the title compound as a colorless oil. Yield 98%.

1H-NMR (400 MHz, CDCl$_3$)δ; 10.17 (1H, br), 5.41 (1H, d, J=5.5 Hz), 4.54–4.44 (2×¼H, m), 3.62 (1H, dd, J=4.5, 13.5 Hz), 2.90 (1H, dd, J=12.0, 13.5 Hz), 2.39–2.26 (2×¾H, m), 2.17 (3×¾H, s), 2.13 (3×¼H, s), 1.96–1.52 (2H, m), 1.15–1.03 (1H, m), 0.92 (3×¾H, d,J=6.5 Hz), 0.90 (3×¼H, d, J=7.0 Hz).

Synthesis Example 5 t-Butyl (2S*, 5S*)-N-acetyl-5-methylpiperidyl-9-carboxylate

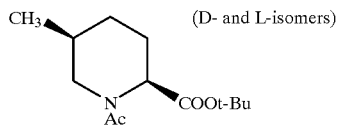

16.3 g (88 mmol) of the (2S*, 5S*)-N-acetyl-5-methylpiperidine-2-carboxylic acid obtained in Synthesis Example 4 was dissolved in 180 ml of dichloromethane, and 6.1 ml (0.11 mol) of concentrated sulfuric acid was added thereto. Then, isobutylene gas was fed into the reaction system, followed by stirring at room temperature for 4 days. The reaction liquid was poured into a saturated aqueous solution of sodium carbonate under cooling with ice, followed by the extraction with chloroform. The organic layer was washed with a saturated aqueous solution of sodium hydrogencarbonate and a saturated aqueous solution of common salt, and then dried over anhydrous sodium sulfate. After filtration, the filtrate was concentrated in a reduced pressure to give 16.4 g of the title compound as a colorless oil. Yield 77%.

1H-NMR (400 MHz, CDCl$_3$)δ; 5.26 (1H, dd, J=1.0, 6.0 Hz), 4.50–4.32 (¾H, m), 3.59 (1H, dd, J=4.5, 13.0 Hz), 2.90 (1H, dd, J=12.0, 13.0 Hz), 2.30–2.17 (⅝H, m), 2.13 (3×¾H, s), 2.07 (3×¼H, s), 1.73–1.56 (2H, m), 1.47 (9×¼H, s), 1.46 (9×¾H, s), 1.05–0.94 (1H, m), 0.91 (3×¾H, d,J=6.5 Hz), 0.90 (3×¼H, d, J=7.0 Hz).

Synthesis Example 6

Methyl (2RS, 4R)-2-[(1S, 4S)-4-acetylamino-4-(t-butoxycarbonyl)-1-methylbutyl]thiazolidine-4-carboxylate and methyl (2RS, 4R)-2-[(1R, 4R)-4-acetylamino-4-(t-butoxycarbonyl)-1-methylbutyl]thiazolidine-4-carboxylate

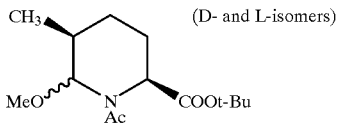

9.41 g (39 mmol) of the t-butyl (2S*, 5S*)-N-acetyl-5-methylpiperidine-2-carboxylate obtained in Synthesis Example 5 was dissolved in 150 ml of methanol, followed by the addition of tetraethylammonium p-toluenesulfonate (Et$_4$NOTs, 1.5 g, 1 w/v %). A constant current (480 mA) was passed through it with carbon electrodes under the conditions of 11.4 F/mol and a current density (60 mA/cm2) at room temperature. After the reaction solution was concentrated in a reduced pressure, the residue was dissolved in ethyl acetate, it was washed with water and a saturated aqueous solution of common salt, and the organic layer was dried over anhydrous sodium sulfate. After filtration, the filtrate was concentrated in a reduced pressure to give 11.5 g of (2S*, 5S*)-N-acetyl-6-methoxy-5-methylpiperidine-2-carboxylate as a crude product.

11.5 g of the above (2S*, 5S*)-N-acetyl-6-methoxy-5-methylpiperidine-2-carboxylate was dissolved in 100 ml of acetic acid-water (1:1), and then 6.0 ml (55 mmol) of N-methylmorpholine and 8.7 g (51 mmol) of methyl L-cysteinate hydrochloride were added thereto, followed by stirring in a nitrogen atmosphere at room temperature for 3 days. The reaction liquid was concentrated to remove the acetic acid. After the extraction with dichloromethane, the organic layer was washed with water and a saturated aqueous solution of common salt, and dried over anhydrous magnesium sulfate. After filtration, the filtrate was concentrated in a reduced pressure and the obtained residue was purified by silica gel column chromatography (eluted with dichloromethane:ethanol=98:2) to give 9.21 g of the title compound as a pale-yellow oil (diastereomeric ratio 1:1:1:1). Yield 63%.

1H-NMR (400 MHz, CDCl$_3$)δ; 6.18–6.04 (1H, m), 4.56–4.36 (2H, m), 4.14–4.04 (2×¼H, m), 3.82–3.68 (2×¼H, m), 3.79 (3×²⁄₄H, s), 3.77 (3×²⁄₄H, s), 3.30–3.25 (2×¼H, m), 3.20–3.16 (2×¼H, m), 3.04–2.97 (2×¼H, m), 2.80–2.70 (2×¼H, m), 2.03 (3×²⁄₄H, s), 2.02 (3×¼H, s), 2.01 (3×¼H, s), 2.00–1.50 (5H, m), 1.482 (9×¼H, s), 1.478 (9×¼H, s), 1.473 (9×¼H, s), 1.470 (9×¼H, s), 1.10 (3×¼H, d, J=7.0 Hz), 1.04 (3×¼H, d, J=7.0 Hz), 1.03 (3×¼H, d, J=7.0 Hz), 0.97 (3×¼H, d, J=7.0 Hz).

Synthesis Example 7

Methyl [3R-(3α, 6α, 9β, 9aβ)]-6-acetylamino-9-methyl-5-oxo-octahydrothiazolo[3,2-a]azepine-3-carboxylate and methyl [3R-(3α, 6α, 9β, 9aβ)]-6-acetylamino-9-methyl-5-oxo-octahydrothiazolo[3,2-a]azepine-3-carboxylate

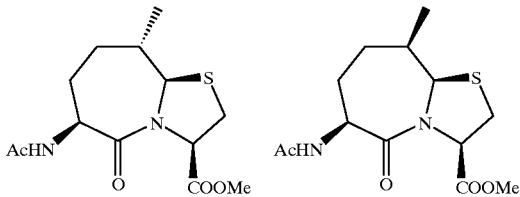

50 ml of trifluoroacetic acid was added to 8.30 g (22.2 mmol) of the mixture of methyl (2RS, 4R)-2-[(1S, 4S)-4-acetylamino-4-(t-butoxycarbonyl)-2-methylbutyl]-thiazolidine-4-carboxylate and methyl (2RS, 4R)-1 -[(1R, 4R)-4-acetylamino-4-(t-butoxycarbonyl)-1-methylbutyl] thiazolidine-4-carboxylate obtained in Synthesis Example 6 under cooling with ice, followed by gradually raising the temperature to room temperature. After stirring for 6 hours, it was distilled to remove the solvent, and azeotropic distillation with toluene was conducted to give 9.84 g of a mixture of trifluoroacetic acid salt of methyl (2R, 4R)-2-[(1S, 4RS)-4-acetylamino-4-(carboxy)-1-methylbutyl]-thiazolidine-4-carboxylate acid and trifluoroacetic acid salt of methyl (2R, 4R)-2-[(1R, 4RS)-4-acetylamino-4-(carboxy-1-methylbutyl]thiazolidine-4-carboxylate (isomeric ratio 1.4:1.4:1:1) as a crude product. 9.84 g of this crude product was dissolved in 150 ml of tetrahydrofuran, followed by the addition of 9.8 ml (89 mmol) of N-methylmorpholine to adjust to pH-7. 2-ethoxy-1-ethoxycarbonyl-1,2-dihydroquinoline (EEDQ, 6.59 g, 27 mmol) was added thereto at room temperature, followed by stirring in a nitrogen atmosphere at room temperature overnight. After concentrating the reaction liquid in a reduced pressure, 100 ml of 2N-hydrochloric acid was added to the residue to adjust to pH 1 or below, followed by the extraction with dichloromethane. The organic layer was washed with a saturated aqueous solution of sodium hydrogencarbonate and a saturated aqueous solution of common salt, and then dried over anhydrous magnesium sulfate. After filtration, the filtrate was concentrated in a reduced pressure, the obtained residue was purified by silica gel column chromatography (eluted with dichloromethane:ethanol=98:2) and 2.59 g of a mixture of the title compounds (isomeric ratio 2:1) was obtained as a white crystal by recrystallization (ethyl acetate-hexane). Yield 39%.

1H-NMR (400 MHz, CDCl3) δ; 6.83–6.74 (1H, m), 5.33 (⅔H, dd, J=3.2, 6.4 Hz), 5.23 (⅓H, s), 4.96 (⅓H, t, J=6.8 Hz), 4.82 (⅔H, d, J=9.5 Hz), 4.60–4.58 (1H, m), 3.79 (3H, s), 3.32 (⅓H, dd, 6.4, 11.6 Hz), 3.22 (⅔H, dd, J=3.2, 11.6 Hz), 3.14 (⅓H, dd, J=6.8, 11.6 Hz), 3.10 (⅔H, dd, J=6.8, 11.6 Hz), 2.01 (3×⅔H, s), 2.00 (3×⅓H, s), 2.10–1.89 (3H, m), 1.80–1.66 (2H, m), 1.12 (3×⅓H, d, J=7.2 Hz), 1.00 (3×⅔H, d, J=6.8 Hz).

Synthesis Example 8

2-Acetyl-decahydro-(4aR-8aR)-isoquinoline-3(S)-carboxylic acid

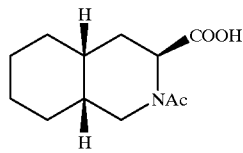

A mixture comprising (4aR, 8aS) isomer, (4aR, 8aR) isomer and trans isomer of decahydroisoquinoline-3(S)-carboxylic acid was dissolved in 72 ml of water, followed by the addition of 60.9 g (725 mmol) of sodium hydrogencarbonate and 72 ml of dichloromethane at room temperature. Thereafter, 27.4 ml (290 mmol) of acetic anhydride was slowly dropwise added thereto, followed by stirring for 22 hours. Insolubles were separated by filtration. After 6N hydrochloric acid was poured thereinto to adjust to pH3, common salt was added thereto up to saturation. Extraction with chloroform was conducted and the organic layer was dried over anhydrous sodium sulfate. After filtration, the filtrate was concentrated in a reduced pressure. Dichloromethane was added thereto to thereby obtain 5.45 g of a crystal of the title compound. Yield 33.4% (two steps).

Synthesis Example 9 t-Butyl 2-acetyl-decahydro-(4aR, 8aR)-isoquinoline-3(S)-carboxylate

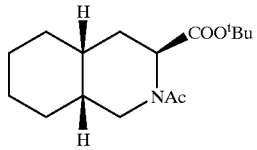

5.21 g of the title compound was obtained with the use of the compound obtained in Synthesis Example 8 in a similar manner to that of Synthesis Example 5. Yield 77%.

Synthesis Example 10

Methyl (2RS, 4R)-2-[(1R, 2R)-2-[(2S)-2-acetylamino-2-(t-butoxycarbonyl)ethyl]cyclohexyl]-thiazolidine-4-carboxylate

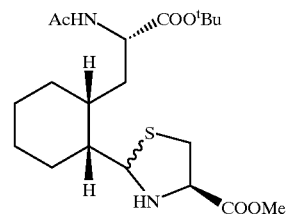

1.61 g of the title compound was obtained with the use of the compound prepared in Synthesis Example 9 in a similar manner to that of Synthesis Example 6. Yield 21%.

1H-NMR (400 MHz, CDCl$_3$) δ; 7.28 and 6.15 (total 1H, each brd), 4.57–3.75 (total 3H, m, 3.78 and 3.76 (total 3H, each s), 3.30–3.20 (total 1H, m), 3.04 and 2.76 (total 1H, dd and t), 2.01 and 1.97 (total 3H, each s), 1.50 and 1.47 (total 9H, each s), 2.40–1.05 (total 12H, m)

Synthesis Example 11

Methyl-(3R, 6R, 7aR, 11aR, 11bR)-6-acetylamino-5-oxo-2-3,5,6,7,7a,11a,11b-octahydrocyclohexyl-[c]thiazolo[3,2-a]azepine-3-carboxylate

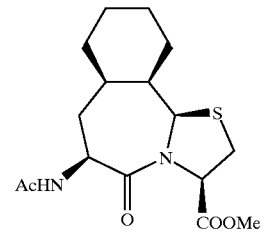

0.48 g of the title compound was obtained with the use of the compound obtained in Synthesis Example 10 in a similar manner to that of Synthesis Example 7. Yield 36%. The absolute configuration was determined on the NOE obtained in NMR spectroscopy.

1H-NMR (400 MHz, CDCl$_3$) δ: 6.76 (1H, brd, J=6.0 Hz), 5.14 (1H, s), 4.91 (1H, t, J=7.0 Hz), 4.56 (1H, ddd, J=1.8, 6.0, 11.4 Hz), 3.79 (3H, s), 3.29 (1H, dd, J=7.0 11.6 Hz), 3.13 (1H, dd, J=7.0, 11.6 Hz), 2.35–2.30 (1H, m), 2.07–1.15 (11H, m), 2.00 (3H, s) NOE δ; 3.29 (H2β)↓→1.70 (H11) 5,14 (H11b)↓→1.85 (H11a ), 2.33 (H7a ), 4.56 (H6) 4.91 (H3)↓→3.13 (H2α) 4.56 (H6)↓→2.33 (H7α)

Synthesis Example 12

A mixture of methyl [3R-(3α, 6α, 8α, 9aβ)]-6-acetylamino-8-methyl-5-oxo-octahydrothiazolo[3,2-a]-azepine-3-carboxylate and methyl [3R-(3α, 6α, 8β, 9aβ)]-6-acetylamino-8-methyl-5-oxo-octahydrothiazolo[3,2-a] azepine-3-carboxylate

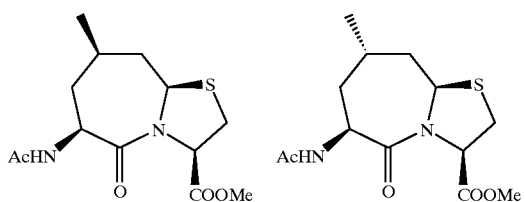

A mixture comprising the above title compounds at a ratio of about 1:1 was synthesized with the use of DL-(2S*, 4S*)-2-carboxy-4-methylpiperidinium chloride in a similar manner to that of Synthesis Example A-4-7.

t-Butyl (S)-N-acetyl-5-formyl-1,2,3,4-tetrahydropyridine-2-carboxylate

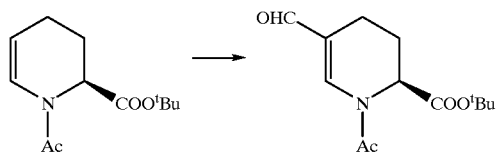

82 mL (880 mmol) of phosphorus oxychloride was added to 137 mL (1.77 mol) of dimethylformamide at 0° C., and then a solution of 39.8 g (177 mmol) of the t-butyl (S)-N-acetyl-1,2,3,4-tetrahydropyridine-2-carboxylate obtained in Synthesis Example 13 in 40 ml of dimethylformamide was added thereto at −10–0° C., followed by gradually raising the temperature to room temperature. After stirring for one hour, the reaction liquid was poured into 2.0 L of an aqueous solution of 365 g (4.49 mol) of sodium sulfate, followed by the extraction with ethyl acetate. The organic layer was washed with a saturated sodium hydrogencarbonate and a saturated aqueous solution of common salt, followed by dring over sodium sulfate. The solvent was removed by distillation, and the residue was recrystallized from isopropyl ether to give 18.1 g of the title compound. Yield 40%.

[0001]

1H-NMR (400 MHz, CDCl3) d; 9.35 (⅛H, s), 9.30 (⅝H, s), 8.16 (⅛H, s), 7.50 (⅝H, s), 5.13 (⅝H, s), 4.62 (⅛H, br), 2.60–2.40 (2H, m), 2.41 (3×⅝H, s), 2.22 (3×⅛H, s), 1.98–1.70 (2H, m), 1.45 (9H, s)

[0001]

Synthesis Example 15
t-Butyl (2S. SS)-N-acetyl-5-methylpiperidine-2-carboxylate

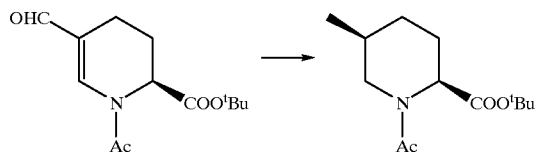

140 mg (0.529 mmol) of the t-butyl (S)-N-acetyl-5-formyl-1,2,3,4-tetrahydropyridine-2-carboxylate obtained in Synthesis Example 14 was dissolved in 20 mL of ethanol, followed by the addition of 5% Pd/C (140 mg). It was treated in a hydrogen atmosphere of 3 kg/cm2 by the use of mediumpressure catalytic reduction equipment to conduct hydrogenation. The catalyst was removed by filtration and the filtrate was concentrated to give 140 mg of the title compound. Yield 100%.

[0001]

Synthesis Example 16 t-Butyl (S)-N-acetyl-5-vinyl-1,2,3,4-tetrahydropyridine-2-carboxylate

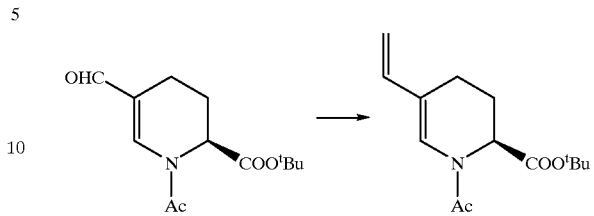

An ethereal solution (42.5 mL) of n-butyllithium was added to a suspended solution of 15.2 g (42.5 mmol) of methyltriphenylphosphonium bromide in diethyl ether (80 ml) at 30° C. or below. To this solution, a THF solution of 8.98 g (35.5 mmol) of the t-butyl (S)-N-acetyl-5-formyl-11, 2,3,4-tetrahydropyridine-2-carboxylate obtained in Synthesis Example 14 at room temperature, followed by stirring overnight. Water was added to the reaction liquid, followed by the extraction with ethyl acetate. After washing with a saturated aqueous solution of common salt, it was dried over sodium sulfate. It was purified by silica gel column chromatography (eluted with n-hexane:ethyl acetate=2:1) to give 4.08 g of the title compound. Yield 46%.

1H-NMR (400 MHz, CDCl3) d; 7.35 (⅛H, s), 6.69 (⅝H, s), 6.38 (⅛H, dd, J=10.8, 17.6 Hz), 6.30 (⅝H, dd, J=10.8, 17.2 Hz), 5.11 (⅝H, m), 5.05 (⅝H, d, J=17.2 Hz), 5.03 (⅛H, d, J=17.6 Hz), 4.95 (⅝H, d, J=10.8 Hz), 4.93 (⅛H, d, J=10.8 Hz), 4.53 (1H, m), 2.52–2.38 (1H, m), 2.34–2.24 (1H, m), 2.26 (3×⅝H, s), 2.14 (3×⅛H, s), 2.04–1.78 (2H, m), 1.45 (9×⅛H, s), 1.44 (9×⅝H, s)

Synthesis Example 17 t-Butyl (2S, 5S)-N-acetyl-5-ethypiperidine-2-carboxylate

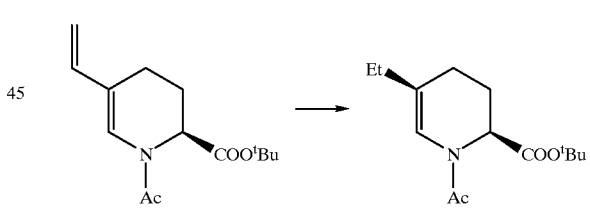

4.08 g (16.3 mmol) of the t-butyl (S)-N-acetyl-5-vinyl-1, 2,3,4-tetrahydropyridine-2-carboxylate obtained in Synthesis Example 16 was dissolved in 150 mL of ethanol, followed by the addition of 4.3 g of 10% Pd/C. It was treated in a hydrogen atmosphere of 3 kg/cm2 by the use of medium pressure catalytic reaction equipment to conduct hydrogenation. The catalyst was removed by filtration and the filtrate was concentrated to give 140 mg of the title compound. Yield 100%.

1H-NMR (400 MHz, CDCl3) d: 5.27 (1H, d, J=6.0 Hz), 4.52–4.35 (¾H, m), 3.64 (1H, dd, J=4.5, 13.0 Hz), 2.91 (1H, dd, J=12.0, 13.0 Hz), 2.35–2.15 (¾H, m), 2.13 (3×¾H, s), 2.07 (3×¼H, s), 1.80–1.50 (2H, m), 1.47 (9×¼H, s), 1.46 (9×¼H, s), 1.35–1.20 (2H, m), 1.05–0.95 (1H, m), 0.93 (3×¾H, t, J=7.6 Hz), 0.90 (3×¼H, t, J=7.6 Hz)

Synthesis Example 18

Methyl (2RS, 4R)-2-[(1S, 4S)-4-acetylamino-4-t-butoxycarbonyl)-1-ethylbutyl]thiazolidine-4-carboxylate

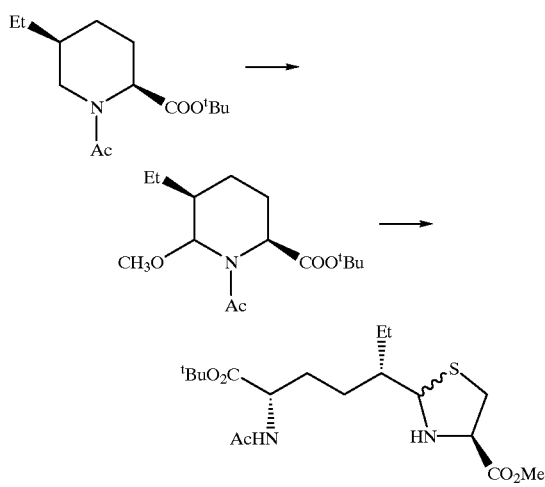

4.29 g (16.8 mmol) of the t-butyl (2S, 5S)-N-acetyl-5-ethylpiperidine-2-carboxylate obtained in Synthesis Example 17 was dissolved in 43 ml of methanol, followed by the addition of 0.43 g of tetraethylammonium tosylate. A constant current (0.33 A) was passed through it with carbon electrodes under the condition of 5 F/mol at room temperature. The reaction solution was concentrated in a reduced pressure and the residue was dissolved in ethyl acetate. It was washed with water and a saturated aqueous solution of common salt and the organic layer was dried over anhydrous sodium sulfate. After filtration, 5.08 g of (2S, 5S)-N-acetyl-6-methoxy-5-methylpiperidine-2-carboxylate of the filtrate was obtained as a crude product. Next, the above crude product was dissolved in 60 mL of acetic acid-water (1:1), and 2.4 mL (23.7 mmol) of N-methylmorpholine and 3.46 g (20.2 mmol) of methyl L-cysteinate hydrochloride was added thereto, followed stirring in a nitrogen atmosphere at room temperature for 3 days. The reaction liquid was poured into an aqueous solution (120 mL) of 49 g of sodium hydrogen-carbonate, followed by the extraction with ethyl acetate. It was washed with a saturated aqueous solution of common salt, and dried over anhydrous sodium sulfate. After filtration, the filtrate was concentrated and the residue was purified by silica gel column chromatography (dichloromethane:ethanol=100:1) to give 3.62 g of the title compound. Yield 55%.

1H-NMR (400 MHz, CDCl3) d; 6.11 (⅔H, d, J=7.6 Hz), 6.06 (⅓H, d, J=8.0 Hz), 4.60 (⅓H, m), 4.55–4.40 (2×⅔H, m), 4.12 (⅓H, m), 3.78 (3×⅔H, s), 3.77 (3×⅓H, s), 3.85–3.70 (1H, m), 3.28 (⅔H, dd, J=7.2, 10.4 Hz), 3.17 (⅓H, dd, J=7.6, 10.8 Hz), 3.03 (⅓H, ⅓H, dd, J=5.6, 10.8 Hz), 2.77 (⅔H, dd, 10.0, 10.4 Hz), 2.02 (3H, s), 1.90–1.20 (7H, m), 1.48 (9×⅓H, s), 1.47 (9×⅔H, s), 0.92 (3×⅔H, t, J=7.6 Hz), 0.90 (3×⅓H, t, J=7.6 Hz), (as a 1:2 diastereomer mixture)

Synthesis Example 19

Methyl [3R-(3α, 6α, 9β, 9aβ)]-6-acetylamino-9-ethyl-5-oxo-octahydrothizolo[3,2-a]azepine-3-carboxylate

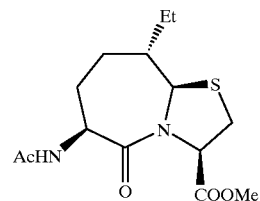

21.5 ml of trifluoroacetic acid was added to 3.62 g (9.31 mmol) of the methyl (2RS, 4R)-2-[(1S, 4S)-4-acetylamino-4-t-butoxycarbonyl)-1-ethylbutyl]-thiazolidine-4-carboxylate obtained in Synthesis Example 18 under cooling with ice, followed by gradually raising the temperature up to room temperature. After stirring for 5 hours, it was distilled to remove the solvent, followed by the azeotropic distillation with toluene to give trifluoroacetic acid salt of methyl (2R, 4R)-2-[(1S, 4RS)-4-acetylamino-4-carboxy-1-ethylbutyl]-thiazolidine-4-carboxylate acid as a crude product. This crude product was dissolved in 60 ml of tetrahydrofuran, followed by the addition of 4.09 ml (37.2 mmol) of N-methylmorpholine to adjust to pH-7. 2-Ethoxy-1-ethoxycarbonyl-1,2-dihydroquinoline (EEDQ, 2.76 g, 11.2 mmol) was added thereto at room temperature, followed by stirring in a nitrogen atmosphere at room temperature overnight. After concentrating the reaction liquid in a reduced pressure, 100 ml of 2N-hydrochloric acid was added to the residue to adjust to pH-1 or below, followed by the extraction with dichloromethane. The organic layer was washed with a saturated aqueous solution of sodium hydrogencarbonate and a saturated aqueous solution of common salt, and then dried over anhydrous magnesium sulfate. After filtration, the filtrate was concentrated in a reduced pressure and the obtained residue was purified by silica gel column chromatography (eluted with dichloromethane:ethanol= 100:1 to 100:3) to give 1.3 g of the title compound as a white crystal. Yield 44%.

1H-NMR (400 MHz, CDCl3) d; 6.80 (1H, br ), 5.30 (1H, dd, J=3.6, 6.8 Hz), 4.87 (1H, d, J=9.2 Hz), 4.58 (1h, m), 3.79 (3H, s), 3.22 (1H, dd, 3.6, 11.6 Hz), 3.10 (1H, dd, J=6.8, 11.6 Hz), 2.18–2.08 (1H, m), 2.01 (3H, s), 1.84–1.56 (5H, m), 1.31 (1H, m), 0.92 (3H, t, J=7.6 Hz)

Example 1

Methyl [3R-3α, 6α, 9α,9aβ)]-6-amino-9-methyl-5-oxo-octahydrothiazolo[32-a]azepine-3-carboxylate and methyl [3R-(3α, 6α, 9α, 9aβ)]-6-amino-9-methyl-5-oxo-octahydrothiazolo[3,2-a]azepine-3-carboxylate

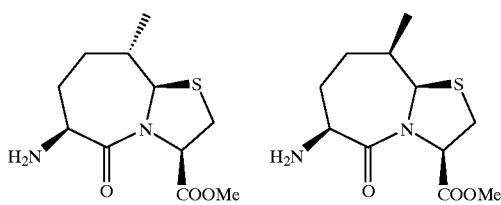

2.59 g (8.6 mmol ) of the mixture (isomeric ratio 2:1) of methyl [3R-(3α, 6α, 9β, 9aβ)]-6-acetylamino-9-methyl-5-oxo-octahydrothiazolo[3,2-a]azepine-3-carboxylate and methyl [3R-(3α, 6α, 9α, 9aβ)]-6-acetylamino-9-methyl-5-oxo-octahydrothiazolo[3,2-a]-azepine-3-carboxylate obtained in Synthesis Example 7 was dissolved in a 10% solution (100 ml) of hydrochloric acid in methanol, followed by heating under reflux for 26 hours. After it was distilled in a reduced pressure to remove the solvent, 2N-hydrochloric acid was added thereto, followed by washing with dichloromethane. After alkalified the aqueous layer with aqueous ammonia, extraction was conducted with dichloromethane, and the organic layer was dried over anhydrous potassium carbonate. After filtration, the filtrate was concentrated in a reduced pressure to give 2.01 g of a mixture of the title compounds (isomeric ratio 2:1) as a colorless oil. Yield 90%.

1H-NMR (400 MHz, CDCl3) d; 5.35 (⅔H, dd, J=3.2, 6.8 Hz), 4.99 (⅓H, t, J=6.8 Hz), 4.76 (⅔H, d, J=10.0 Hz), 4.78–4.70 (⅓H, m), 3.78 (3×⅔H, s), 3.76 (3×⅓H, s), 3.55 (⅔H, dd, J=2.2, 10.6 Hz), 3.49 (⅓H, dd, J=2.0, 10.8 Hz), 3.30 (⅓H, dd, J=6.0, 11.6 Hz), 3.21 (⅔H, dd, J=3.2, 12.0 Hz), 3.11 (⅓H, dd, J=7.2, 11.8 Hz), 3.09 (⅔H, dd, J=6.4, 12.0 Hz), 2.12–1.50 (7H, m), 1.12 (3×⅓H, d, J=6.8 Hz), 1.00 (3×⅔H, d, J=6.8 Hz).

Example 2

Methyl [3R-(3α, 6α, 9β, 9aβ)]-6-[[(2S, 3S)-1-oxo-2-acetylthio-3-methylpentyl]amino]-9-methyl-5-oxo-octahydrothiazolo [3,2-a]azepine-3-carboxylate and methyl [3R-(3α, 6α, 9α, 9aβ]-6-[[(2S,3S)-1-oxo-2-acetylthio-3-methylpentyl]amino]-9-methyl-5-oxo-octahydrothiazolo[3,2-a]azepine-3-carboxylate

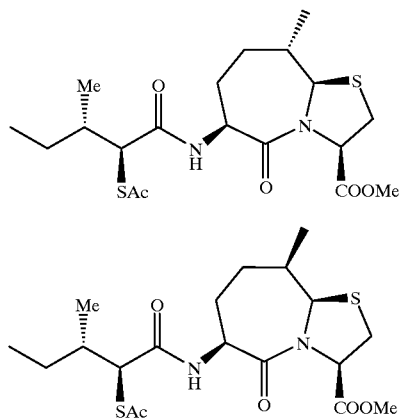

A solution of 1.78 g (9.3 mmol) of (2S, 3S)-2-acetylthio-3-methylpentanoic acid in tetrahydrofuran (100ml) was added to 2.01 g (7.8 mmol) of the mixture (isomeric ratio 2:1) of methyl [3R-(3α, 6α, 9β, 9aβ)]-6-amino-9-methyl-5-oxo-octahydrothiazolo[3,2-a]azepine-3-carboxylate and methyl [3R-(3α,6α, 9β,9aβ)]-6-amino-9-methyl-5-oxo-octahydrothiazolo[3,2-a]azepine-3 -carboxylate obtained in Example 1 under cooling with ice. 1.79 g (9.3 mmol) of 1-ethyl-3-(3-dimethylaminopropyl)carbodiimide hydrochloride (DEC HCl), 1.03 ml (9.3 mmol) of N-methylmorpholine and 1.26 g (9.3 mmol) of 1-hydroxy-1H-benzotriazole monohydrate (HOBT) were added to this solution successively, followed by stirring in a nitrogen atmosphere at room temperature for 18 hours. After the addition of water and the extraction with ethyl acetate, the organic layer was washed with 1N-hydrochloric acid, a saturated aqueous solution of sodium hydrogencarbonate and a saturated aqueous solution of common salt, and dried over anhydrous magnesium sulfate. After filtration, the filtrate was concentrated in a reduced pressure and the obtained residue was purified by silica gel column chromatography (eluted with hexane:ethyl acetate=3:1). 837 mg of Methyl [3R-(3α, 6α, 9β, 9aβ)]-6-[[(2S, 3S)-1-oxo-2-acetylthio-3-methylpentyl]amino]-9-methyl-5-oxo-octahydrothiazolo[3,2-a]azepine-3-carboxylate as a colorless oil was recovered as the first effluent. Yield 42%. The absolute configuration of the compound was determined by the NOE experiment.

1H-NMR (400 MHz, CDCl3) d; 7.37 (1H, d, J=6.0 Hz), 5.36 (1H, dd, J=3.0, 7.0 Hz), 4.80 (1H, d, J=9.5 Hz), 4.53 (1H, m), 3.97 (1H, d, J=7.0 Hz), 3.79 (3H, s), 3.22 (1H, dd, J=3.0, 11.5 Hz), 3.10 (1H, dd, J=7.0, 11.5 Hz), 2.38 (3H, s), 2.14–1.90 (3H, m), 1.78–1.62 (3H, m), 1.57 (1H, m), 1.16 (1H, m), 1.00 (3H, d, J=6.5 Hz), 0.99 (3H, d, J=7.0 Hz), 0.88 (3H, t, J=7.5 Hz). NOE δ; 1.00 (9-Me )↓→4.80 (H9a 3.10 (H2α)↓→4.80 (H9a), 5.36 (H3) 3.22 (H2β)↓→1.95 (H9), 3.79 (3-COOMe), 4.53 (H6)↓→4.80 (H9a

Further, 532 mg of methyl [3R-(3α, 6α, 9α, 9aβ)]-6-[[(2S, 3S)-1-oxo-2-acetylthio-3-methylpentyl]amino]-9-methyl-5-oxo-octahydrothiazolo[3,2-a]azepine-3-carboxylate as a colorless oil was recovered as the second effluent. Yield 16%. The absolute configuration of the compound was determined by the NOE experiment.

1H-NMR (400 MHz, CDCl3) d; 7.32 (1H, brd, J=6.1 Hz), 5.20 (1H, s), 5.00 (1H, dd, J=6.0, 6.4 Hz), 4.48 (1H, m), 3.96 (1H, d, J=6.6 Hz), 3.78 (3H, s), 3.32 (1H, dd, J=6.0, 11.7 Hz), 3.13 (1H, dd, J=6.4, 11.7 Hz), 2.37 (31H, s), 2.20–1.50 (7H, m), 1.15 (1H, m), 1.10 (3H, d, J=7.4 Hz), 0.98 (3H, d, J=6.8 Hz), 0.87 (3H, t, J=7.2 Hz). NOE δ; 1.10 (9-Me )↓→3.32 (H2β), 3.78(3-COOMe ), 3.13 (H2α)↓→5.20 (H9a) 5.00 (H3) 4.48 (H6)↓→5.20 (H9a Example 3

[3R, (3α,6α, 9β, 9aβ)]-6-[-(2S, 3S)-1-Oxo-2-thio-3-methylpentyl]amino]-9-methyl-5-oxo-octahydrothiazolo[3,2-a]azepine-3-carboxylic acid

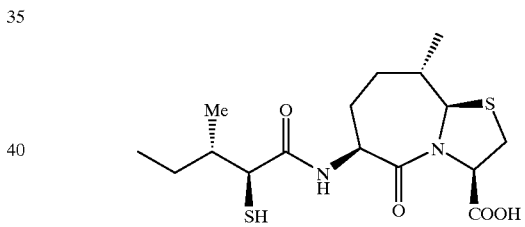

167 mg (0.39 mmol) of the methyl [3R-(3α, 6α, 9β, 9aβ)]-6-[[(2S, 3S)-1-oxo-2-acetylthio-3-methylpentyl]-amino]-9-methyl-5-oxo-octahydrothiazolo[3,2-a]-azepine-3-carboxylate obtained in Example 2 was dissolved in 5 ml of deaerated ethanol, 2.0 ml (2.0 mmol) of a 1N-aqueous solution of lithium hydroxide was added thereto under cooling with ice, followed by stirring in a nitrogen atmosphere at room temperature for one hour. The reaction solution was acidified by adding 7.5 ml of 2N-hydrochloric acid thereto under cooling with ice. After the dilution thereof with water, extraction was conducted with dichloromethane. The organic layer was washed with a saturated aqueous solution of common salt, and dried over anhydrous magnesium sulfate. After filtration, the filtrate was concentrated in a reduced pressure. The obtained amorphous was recrystallized (dichloromethane-hexane) and it was dried with hot air at 50° C. for 12 hours to give 118 mg of the title compound as a white crystal. Yield 81%.

1H-NMR (400 MHz, CDCl3) d; 7.66 (1H, d, J=6.5 Hz), 5.39 (1H, dd, J=3.0, 7.0 Hz), 4.86 (1H) d, J=9.5 Hz), 4.60 (1H, m), 3.29 (1H, dd, J=3.0, 12.0 Hz), 3.22 (1H, dd, J=7.0, 9.0 Hz), 3.13 (1H, dd, J=7.0, 12.0 Hz), 2.10–1.90 (4H, m), 1.87 (1H, d, J=9.0 Hz), 1.81–1.64 (2H, m), 1.61 (1H, m), 1.21 (1H, m), 1.03 (3H, d, J=7.0 Hz), 1.00 (3H, d, J=7.0 Hz), 0.90 (3H, t, J=7.0 Hz).

Example 4

Methyl (3R, 6S, 7aR, 11aR, 11bR)-6-amino-5-oxo-2,3,5, 6,7,7a, 11a, 11b-octahydrocyclohexyl[c]thiazolo-[3,2-a] azepine-3-carboxylate

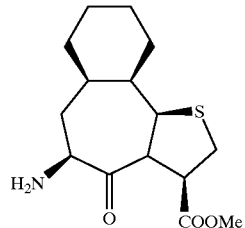

0.23 g of the title compound was obtained with the use of the compound obtained in Synthesis Example 11 in a similar manner to that of Example 1. Yield 57%. 1H-NMR (400 MHz, CDCl$_3$)δ; 5.08 (1H, s), 4.94 (1H, t, J=6.8 Hz), 3.78 (3H, s), 3.54–3.52 (1H m) 3.27 (1H, dd, J=6.8, 11.6 Hz), 3.11 (1H, dd, J=6.8, 11.6 Hz), 2.23–1.18 (14H, m)

Example 5

Methyl (3R, 6R, 7aR, 11aR, 11bR)-6-[[(2S, 3S)-1-oxo-2-acetylthio-3-methylpentyl]amino]-5-oxo-2,3,5,6,7a,11a, 11b-octahydrocyclohexyl[c]thiazolo[3,2-a]azepine-3-carboxylate

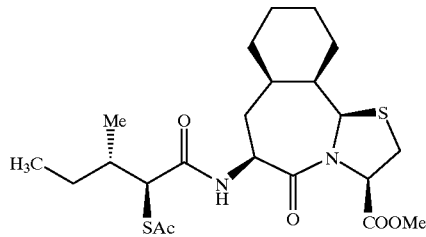

0.32 g of the title compound was obtained with the use of the compound obtained in Example 4 in a similar manner to that of Example A. Yield 88%.

1H-NMR (400 MHz, CDCl$_3$)δ; 7.33 (1H, brd, J=6.0 Hz), 5.14 (1H, s), 4.96 (1H, t, J=6.6 Hz), 4.57–4.52 (1H, m), 3.97 (1H, d, J=6.8 Hz), 3.79 (3H, s), 3.30 (1H, dd, J=6.6, 11.6 Hz), 3.14 (1H, dd, J=6.6, 11.6 Hz), 2.38 (3H, s), 2.40–0.85 (15H, m), 0.99 (3H, d, J=6.8 Hz) 0.89 (3H, t, J=7.4 Hz)

Example 6

(3R, 6R, 7aR, 11aR, 11bR)-6-[[(2S, 3)-1-Oxo-9-thio-3-methylpentyl]amino]-5-oxo-2,3,5,6,7,7a, 11a,11b-octahydrocyclohexyl[c]thiazolo[3,2-a]azepine-3-carboxylic acid

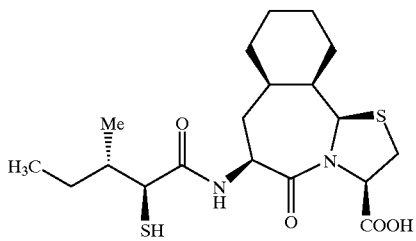

0.18 g of the title compound was obtained as a white crystal with the use of the compound obtained in Example 5 in a similar manner to that of Example 3. Yield 63%.

1H-NMR (400 MHz CDCl$_3$)δ; 7.33 (1H, brd, J=6.0 Hz), 5.14 (1H, s), 4.96 (1H, t, J=6.6 Hz), 4.57–4.52 (1H, m), 3.97 (1H, d, J=6.8 Hz), 3.79 (3H, s), 3.30 (1H, dd, J=6.6, 11.6 Hz), 3.14 (1H, dd, J=6.6, 11.6 Hz), 2.38 (3H, s), 2.40–0.85 (15H, m), 0.99 (3H, d, J=6.8 Hz), 0.89 (3H, t, J=7.4 Hz)

Example 7

Methyl [3R-(3α, 6α, 8α, 9aβ)]-6-amino-8-methyl-5-oxo-octahydrothiazolo[3,2-a]azepine-3-carboxylate and methyl [3R-(3α, 6α, 8β, 9aβ)]-6-amino-8-methyl-5-oxo-octahydrothiazolo[3,2-a]azepine-3-carboxylate

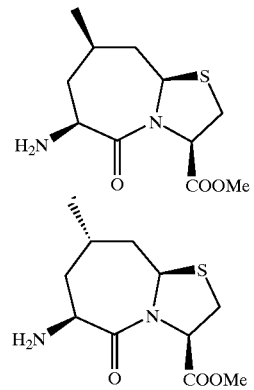

940 mg (3.12 mmol) of the mixture, at about 1:1, of methyl [3R-(3α, 6α, 9α, 9aβ)]-6-acetylamino-8-methyl-5-oxo-octahydrothiazolo[3,2-a]azepine-3-carboxylate and methyl [3R-(3α, 6α, 8β, 9aβ)]-6-acetylamino-8-methyl-5-oxo-octahydrothiazolo[3,2-a]-azepine-3-carboxylate which had been obtained in Synthesis Example 12 was dissolved in 24 ml of a 10% solution of hydrochloric acid in methanol, followed by heating under reflux for 24 hours. After it was distilled in a reduced pressure to remove the solvent, water was added thereto, followed by washing with dichloromethane. The obtained aqueous layer was alkalified by adding a saturated aqueous solution of sodium hydrogencarbonate thereto, and then it was extracted with dichloromethane, followed by drying over anhydrous sodium sulfate. The residue obtained by concentrating it was purified by silica gel column chromatography (chloroform:methanol:aqueous ammonia=98:2:0.2) to give 220 mg of a mixture of two title compounds at about 1.4:1. Yield 27%.

1H-NMR (400 MHz CDCl3) δ; 5.29 (1H×1.4/2.4, dd, J=2.4, 6.4 Hz), 5.00 (1H×1.4/2.4, d, J=10.4 Hz), 3.78 (3H×1.4/2.4, s), 3.54 (1H×1.4/2.4, dd, J=1.2, 10.8 Hz), 3.26 (1H×1.4/2.4, dd, J=2.4 11.6 Hz), 3.17 (1H×1.4/2.4, dd,

J=6.4, 11.6 Hz), 1.43–2.05 (7H×1.4/2.4, m), 1.00 (3H×1.4/2.4, d, J=6.8 Hz)
and

1H-NMR (400 MHz, CDCl3) δ; 5.21 (1H×1.0/2.4, dd, J=3.2, 6.4 Hz), 5.15 (1H×1.0/2.4, dd, J=2.2, 10.2 Hz), 3.78 (3H×1.0/2.4, s), 3.71 (1H×1.0/2.4 dd, J=3.2, 10.8 Hz), 3.27 (1H×1.0/2.4, dd, J=3.2, 12.0 Hz), 3.18 (1H×1.0/2.4, dd, J=6.4, 12.0 Hz), 1.60–2.33 (7H×1.0/2.4, m), 1.16 (3H×1.0/2.4, d, J=7.2 Hz)

Example 8

Methyl [3R-(3α, 6α, 8β, 9aβ)]-6-[[(29S, 3S)-1-oxo-2-acetylthio-3-methylpentyl]amino]-8-methyl-5-oxo-octahydrothiazolo[3,2-a]azepine-3-carboxylate and methyl [3R-(3α, 6α, 8β9a β)-6-[[(2S, 3S)-1-oxo-2-acetylthio-3-methylpentyl]amino]-8-methyl-5-oxo-octahydrothiazolo[3,2-a]azepine-3-carboxylate

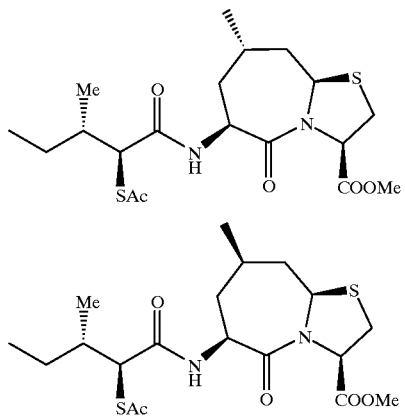

A solution of 214 mg (1.12 mmol) of (2S, 3S)-2-acetylthio-3-methylpentanoic acid in tetrahydrofuran (17 ml) was added to 215 mg (0.83 mmol) of the mixture (isomeric ratio 1:1.4) of methyl [3R-(3α, 6α, 8β, 9aβ)]-6-amino-8-methyl-5-oxo-octahydrothiazolo[3,2-a]-azepine-3-carboxylate and methyl [3R-(3α, 6α, 8β, 9aβ)]-6-amino-8-methyl-5-oxo-octahydrothiazolo[3,2-a]-azepine-3-carboxylate which had been obtained in Example 7 under cooling with ice. To this solution, 207 mg (1.08 mmol) of 1-ethyl-3-(3-dimethylaminopropyl)-carbodiimide hydrochloride (DEC-HCl), 0.12 ml (1.08 mmol) of N-methylmorpholine and 166 mg (1.08 mmol) of 1-hydroxy-1H-benzotriazole monohydrate (HOBT) were added successively, followed by stirring in a nitrogen atmosphere at room temperature for 18 hours. The reaction solution was concentrated, water was added thereto, and it was extracted with ethyl acetate. Thereafter, the organic layer was washed with 1N-hydrochloric acid, a saturated aqueous solution of sodium hydrogencarbonate and a saturated aqueous solution of common salt, and dried over anhydrous magnesium sulfate. After filtration, the residue obtained by concentrating the filtrate in a reduced pressure was purified by silica gel column chromatography (eluted with hexane:ethyl acetate=3:1) to give 254 mg of a mixture (isomeric ratio 1:1.3) of two title compounds. Further, this mixture was placed on a preparative column, YMC-Pack SIL (SH-043-5) (eluted with hexane:ethyl acetate=4:1) to separate and purify. Thus, 97 mg of methyl [3R-(3α, 6α, 8β, 9aβ)]-6-[[(2S, 3S)1-oxo-2-acetylthio-3-methylpentyl]-amino]-8-methyl-5-oxo-octahydrothiazolo[3,2-a]azepine-3-carboxylate) was obtained as a colorless oil from the first effluent. Yield 27%. The absolute configuration of the compound was determined by the NOE experiment.

1H-NMR (400 MHz, CDCl3) δ; 7.26 (1H, brd, J=6.1 Hz), 5.21 (1H, dd, J=2.9, 6.6 Hz), 5.20 (1H, dd, J=1.5, 10.6 Hz), 4.75 (1H, ddd, J=5.0, 6.1, 9.0 Hz), 3.95 (1H, d, J=7.1 Hz), 3.79 (3H, s), 3.28 (1H, dd, J=2.9, 12.0 Hz), 3.20 (1H, dd, J=6.6, 12.0 Hz), 2.37 (3H, s), 2.30–1.10 (8H, m), 1.26 (3H, d, J=7.1 Hz), 0.99 (3H, d, J=6.6 Hz), 0.88 (3H, t, J=7.4 Hz) NOE δ; 1.26 (8-Me )↓→4.75 (H6α), 5.20 (H9aα), 1.68 (H9α), 5.20 (H9aα)↓→1.68 (H9α), 4.75 (H6α), 2.28 (H8β)↓→1.68 (H9α) 136 mg of methyl [3R-(3α, 6α, 8α, 9aβ)]-6-[[(2S, 3S)-1-oxo-2-acetylthio-3-methylpentyl]amino]-8-methyl-5-oxo-octahydrothiazolo[3,2-a]azepine-3-carboxylate was obtained as a colorless oil from the second effluent. Yield 38%. The absolute configuration of the compound was determined by the NOE experiment.

1H-NMR (400 MHz, CDCl3) δ; 7.38 (1H, brd, J=6.0 Hz 5.27 (1H, dd, J=2.4, 6.4 Hz), 5.03 (1H, d, J=10.4 Hz), 4.55 (1H, dd J=6.4, 10.0 Hz), 3.97 (1H, d, J=6.8 Hz), 3.79 (3H, s), 3.27 (1H, dd, J=2.4, 11.8 Hz), 3.19 (1H, dd, J=6.4, 11.8 Hz), 2.38 (3H, s), 2.15–1.11 (8H, m), 0.99 (6H, d J=6.8 Hz), 0.89 (3H, t J=7.4 Hz) NOE δ; 2.09 (H9a)↓→1.88 (H9α), 1.92 (H7α), 4.55 (H6), 5.03 (H9a) 5.03 (H9a )↓→1.88 (H9α), 4.55 (H6) 4.55 (H6)↓→1.92 (H7α)

Example 9

[3R-(3α, 6α, 8α, 9aβ)]-6-[[(2S , 3S)-1-Oxo-2-thio-3-methylpentyl]amino]-8-methyl-octahydro-5-oxothiazolo[3,2-a]azepine-3-carboxylic acid

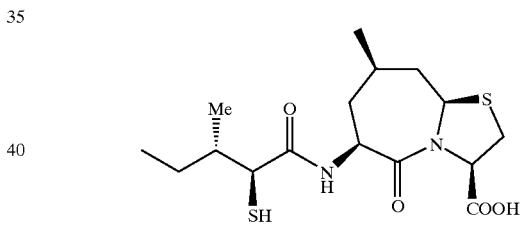

130 mg (0.30 mmol) of the methyl [3R-(3α, 6α, 8α, 9aα)]-6-[[(2S, 3S)-1-oxo-2-acetylthio-3-methylpentyl]amino]-8-methyl-octahydro-5-oxothiazolo[3,2-a]azepine-3-carboxylate obtained in Example 8 was dissolved in 4.3 ml of deaerated EtOH. Next, 2.1 ml of a 1N-aqueous solution of lithium hydroxide was added thereto under cooling with ice, followed by stirring in a nitrogen atmosphere at room temperature for one hour. After it was acidified by adding 1.5 ml of 2N-hydrochloric acid thereto under cooling with ice, water was added thereto, followed by the extraction with dichloromethane. After washing with a saturated aqueous solution of common salt, it was dried over anhydrous magnesium sulfate and concentrated in a reduced pressure. The obtained amorphous was recrystallized (ethyl acetate-hexane) and dried with hot air at 50° C. for 24 hours to give 90 mg of the title compound. Yield 80%.

1H-NMR (400 MHz, CDCl3) δ; 7.61 (1H, brd, J=6.4 Hz ), 5.29 (1H, dd, J=2.4, 6.4 Hz), 5.07 (1H, d J=10.4 Hz), 4.62 (1H, dd, J=6.8, 11.2 Hz), 3.37 1H, dd, J=2.4, 12.0 Hz), 3.22 (1H, dd, J=6.4, 8.8 Hz), 3.21 (1H, dd, J=6.4, 12.0 Hz) 2.19–1.18 (8H, m), 1.87 (1H, d, J=8.8 Hz 1.01 (3H, d, J=6.4 Hz), 1.00 (3H, d, J=6.8 Hz 0.91 (3H, t, J=7.4 Hz)

Example 10

[3R-(3α, 6α, 8β, 9aβ)]-6-[[(2S, 3S)-1-Oxo-2-thio-3-methylpentyl]amino]-8-methyl-octahydro-5-oxothiazolo[3,2-a]azepine-3-carboxylic acid

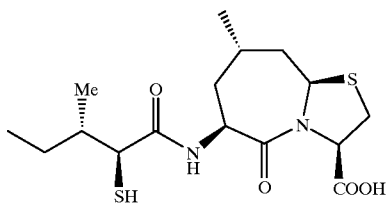

93 mg (0.216 mmol) of the methyl [3R-(3α, 6α, 8β, 9aβ)]-6-[[(2S, 3S)-1-oxo-2-acetylthio-3-methylpentyl]-amino]-8-methyl-octahydro-5-oxothiazolo[3,2-a]-azepine-3-carboxylate obtained in Example 8 was dissolved in 3.1 ml of deaerated EtOH. Next, 1.5 ml of a 1N-aqueous solution of lithium hydroxide was added thereto under cooling with ice, followed by stirring in a nitrogen atmosphere at room temperature for one hour. After it was acidified by adding 1.1 ml of 2N-hydrochloric acid thereto under cooling with ice, water was added thereto, followed by the extraction with dichloromethane. After washing with a saturated aqueous solution of common salt, it was dried over anhydrous magnesium sulfate and concentrated in a reduced pressure. The obtained amorphous was recrystallized (dichloromethane-hexane) and dried with hot air at 50° C. for 24 hours to give 66 mg of the title compound. Yield 82%.

1H-NMR (400 MHz, CDCl3) δ; 7.49 (1H, brd, J=6.0 Hz), 5.27–5.21 (2H, m), 4.84–4.77 (1H, m), 3.37 (1H, dd, J=2.4, 12.0 Hz), 3.22 (1H, dd, J=7.0, 12.0 Hz), 3.19 (1H, dd, J=7.2, 8.8 Hz), 1.88 (1H, d, J=8.8 Hz), 2.33–1.58 (7H, m), 1.28 (3H, d, J=7.2 Hz), 1.30–1.18 (1H, m), 1.00 (3H, d, J=6.8 Hz), 0.90 (3H, t, J=7.2 Hz)

Example 11

[3R-(3α, 6α, 9α, 9aβ)]-6-[[(2S, 3S)-1-Oxo-2-thio-3-methylpentyl]amino]-9-methyl-5-oxo-octahydrothiazolo[3,2-a]azepine-3-carboxylic acid

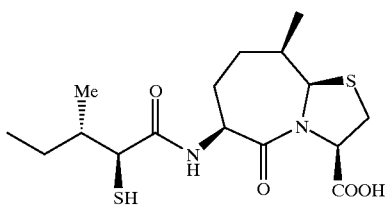

1.43 g (3.33 mmol) of the methyl [3R-(3α, 6α, 9α, 9aβ)]-6-[[(2S, 3S)-1-oxo-2-acetylthio-3-methylpentyl]-amino]-9-methyl-5-oxo-octahydrothiazolo[3,2-a]-azepine-3-carboxylate obtained in Example 2 was dissolved in 30 ml of deaerated ethanol, and 20 ml (20 mmol) of a 1N-aqueous solution of lithium hydroxide was added thereto under cooling with ice, followed by stirring in a nitrogen atmosphere at room temperature for one hour. The reaction solution was acidified by adding 50 ml of 2N-hydrochloric acid thereto under cooling with ice and diluted with water, followed by the extraction with dichloromethane. The organic layer was washed with a saturated aqueous solution of common salt and dried over anhydrous magnesium sulfate. After filtration, the filtrate was concentrated in a reduced pressure. The obtained amorphous was recrystallized (dichloromethane-hexane) and it was dried with hot air at 50° C. for 12 hours to give 1.10 g of the title compound as a white cystal. Yield 89%.

1H-NMR (400 MHz, CDCl3) d; 7.57 (1H, brd, J=6.4 Hz), 5.25 (1H, s), 5.08 (1H, dd, J=3.2, 6.8 Hz), 4.60 (1H, m), 3.48 (1H, dd, J=3.2, 11.6 Hz), 3.25 (1H, dd, J=6.4, 8.4 Hz), 3.13 (1H, dd, J=6.8, 11.6 Hz), 2.16–1.54 (7H, m), 1.85 (1H, d, J=8.4 Hz), 1.24 (1H, m), 1.03 (3H, d, J=6.4 Hz), 1.01 (3H, d, J=6.4 Hz), 0.91 (3H, t, J=7.2 Hz).

Example 12

[3R-(3α,6α, 9β, 9aβ)]-6-[[(2S, 3S-1-Oxo-9-acetylthio-3-methylpentyl]amino]-9-methyl-5-oxo-octahydrothiazolo[3,2-a]azepine-3-carboxylic acid

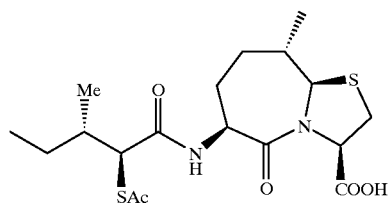

522 mg (1.39 mmol) of the [3R-(3α, 6α, 9β, 9aβ)]-6-[[(2S, 3S)-1-oxo-2-thio-3-methylpentyl]amino]-9-methyl-5-oxo-octahydrothiazolo[3,2-a]azepine-3-carboxylic acid obtained in Example 3 was dissolved in acetonitrile (15 ml)-tetrahydrofuran (15 ml). 54 mg (0.42 mmol) of anhydrous cobalt chloride and 170 ml (1.81 mmol) of acetic anhydride were added thereto at room temperature in a nitrogen atmosphere, followed by stirring for 5 hours. Water was added to the reaction solution, followed by the extraction with ethyl acetate. The organic layer was washed with a saturated aqueous solution of common salt and dried over anhydrous magnesium sulfate. After filtration, the filtrate was concentrated in a reduced pressure. The obtained amorphous was recrystallized (ethyl acetate-hexane) and it was dried with hot air at 50° C. for 18 hours to give 439 mg of the title compound as a white crystal. Yield 76%.

1N-NMR (400 MHz, CDCl3) d; 7.38 (1H, brd, J=6.0 Hz), 5.39 (1H, dd, J=2.8, 6.4 Hz), 4.83 (1H, d, J=9.6 Hz), 4.56 (1H, m), 3.96 (1H, d, J=6.8 Hz), 3.29 (1H, dd, J=2.8, 11.6 Hz), 3.12 (1H, dd, J=6.4, 11.6 Hz), 2.38 (3H, s), 2.14–1.88 (4H, m), 1.77–1.64 (2H, m), 1.58 (1H, m), 1.16 (1H, m), 1.01 (3H, d, J=7.2 Hz), 1.00 (3H, d, J 6.8 Hz), 0.88 (3H, t, J=7.2 Hz).

Example 13

[3R-(-3α, 6α, 9β, 9aβ)]-6-[[(2S, 3S)-1-Oxo-2-propionylthio-1-methylpentyl]amino]-9-methyl-5-oxo-octahydrothiazolo[3,2-a]azepine-3-carboxylic acid

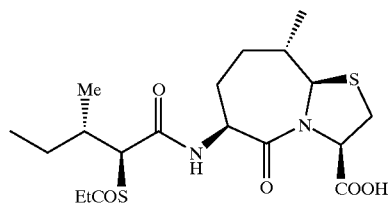

30 mg of the title compound was obtained as a white crystal from 60 mg (0.16 mmol) of the [3R-(3α, 6α, 9β, 9aβ)]-6-[[(2S, 3S)-1-oxo-2-thio-3-methylpentyl]amino]-9-methyl-5-oxo-octahydrothiazolo[3,2-a] azepine-3-carboxylic acid obtained in Example A-3. 17 ml (0.19 mmol) of propionyl chloride and 6 mg (0.05 mmol) of anhydrous cobalt chloride in a similar manner to that of Example 12. Yield 44%.

1H-NMR (400 MHz, CDCl3) d; 7.40 (1H, brd, J=6.4 Hz), 5.39 (1H, dd, J=2.4, 6.8 Hz), 4.83 (1H, d, J=9.6 Hz), 4.56 (6H, m), 3.98 (1H, d, J=6.8 Hz), 3.29 (1H, dd, J=2.8, 11.6 Hz), 3.11 (1H, dd, J=6.8, 11.6 Hz), 2.63 (2H, q, J=7.6 Hz), 2.16–1.88 (4H, m), 1.76–1.64 (2H, m), 1.57 (1H, m), 1.19 (3H, t, J=7.6 Hz), 1.17 (1H, m), 1.01 (3H, d, J=6.8 Hz), 1.00 (3H, d, J=6.8 Hz), 0.88 (3H, t, J=7.2 Hz).

Example 14

[3R-(3α, 6α, 9β, 9aβ)]-6-[[(2S, 3S)-1-Oxo-2-benzoylthio-3-methylpentyl]amino]-9-methyl-5-oxo-octahydrothiazolo[3,2-a]azepine-3-carboxylic acid

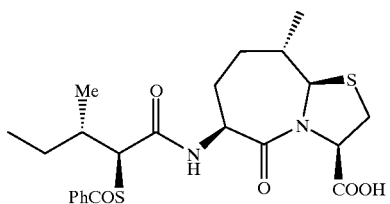

490 mg of the title compound was obtained as a white crystal from 434 mg (1.16 mmol) of the [3R-(3α, 6α, 9β, 9aβ)]-6-[[(2S, 3S)-1-oxo-2-thio-3-methylpentyl]amino]-9-methyl-5-oxo-octahydrothiazolo[3,2-a]azepine-3-carboxylic acid obtained in Example A-3. 300 mg (1.33 mmol) of benzoic anhydride and 45 mg (0.35 mmol) of anhydrous cobalt chloride in a similar manner to that of Example 12. Yield 88%.

1H-NMR (400 MHz, CDCl3) d; 8.00–7.96 (2H, m), 7.62–7.42 (4H, m), 5.38 (1H, dd, J=2.4, 6.4 Hz), 4.84 (1H, d, J=9.6 Hz), 4.59 (1H, m), 4.20 (1H, d, J=7.2 Hz), 3.27 (1H, dd, J=2.4, 11.6 Hz), 3.10 (1H, dd, J=6.4, 11.6 Hz), 2.22–1.60 (7H, m), 1.25 (1H, m), 1.06 (3H, d, J=6.8 Hz), 1.00 (3H, d, J=6.8 Hz), 0.92 (3H, t, J=7.2 Hz).

Example 15

[3R-(3α, 6α, 9β, 9aβ)]-6-[[(2S, 3S)-1-Oxo-2-(1,1-dimethylpropionyl)thio-3-methylpentyl]amino]-9-methyl-5-oxo-octahydrothiazolo[3,2-a]azepine-3-carboxylic

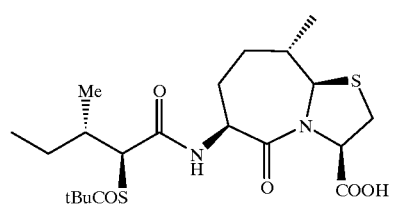

58 mg of the title compound was obtained as a white crystal from 54 mg (0.14 mmol) of the [3R-(3α, 6α, 9α, 9aα)]-6-[[(2S, 3S)-1-oxo-2-thio-3-methylpentyl]-amino]-9-methyl-5-oxo-ocatahydrothiazolo[3,2-a]-azepine-3-carboxylic acid obtained in Example A-3, 27 ml (0.22 mmol) of pivaloyl chloride and 6 mg (0.05 mmol) of anhydrous cobalt chloride in a similar manner to that of Example 12. Yield 88%.

1H-NMR (400 MHz, CDCl3) d; 7.41 (1H, brd, J=6.0 Hz), 5.39 (1H, dd, J=2.4. 6.4 Hz), 4.83 (1H. d. J=9.6 Hz), 4.56 (1H, m), 3.92 (1H, d, J=6.8 Hz), 3.29 (1H, dd, J=2.4, 11.6 Hz), 3.10 (1H, dd, J=6.4, 11.6 Hz), 2.18–1.52 (7H, m), 1.25 (9H, s), 1.20 (1H, m), 1.01 (3H, d, J=6.8 Hz), 1.00 (3H, d, J=6.8 Hz), 0.87 (3H, t, J=7.2 Hz).

Example 16

[3R-(3α, 6α, 9β, 9aβ)]-6-[[(2S, 3S)-1-Oxo-2-(4-morpholinyl)acetylthio-3-methylpentyl]amino]-9-methyl-5-oxo-octahydrothiazolo[3,2-a]azepine-3-carboxylic acid

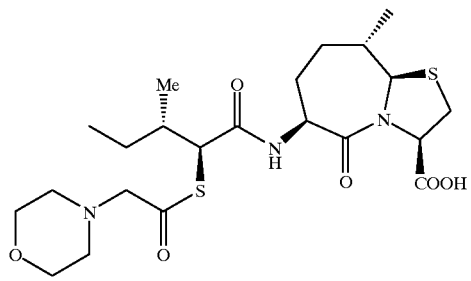

44 mg (0.24 mmol) of 4-morpholinylacetic acid hydrochloride was dissolved in deaerated anhydrous N,N-dimethylformamide (1.2 ml) in a nitrogen atmosphere, and then 27.3 mg (1.68 mmol) of N,N'-carbodiimidazole was added thereto under cooling with ice, followed by stirring at room temperature for one hour. A solution in deaerated, dry tetrahydrofuran (1.6 ml) of 60 mg (0.16 mmol) of the [3R-(3α, 6α, 9β, 9aβ)]-6-[[(2S, 3S)-1-oxo-2-thio-3-methylpentyl]-amino]-9-methyl-5-oxo-octahydrothiazolo [3,2-a]-azepine-3-carboxylic acid obtained in Example 3 was added thereto under cooling with ice, followed by further stirring at room temperature for 2 days. After the reaction solution was concentrated, ethyl acetate and a saturated aqueous solution of common salt was added thereto, thus causing liquid—liquid separation. The organic layer was washed with a saturated aqueous solution of common salt, followed by drying over anhydrous magnesium sulfate. After filtration, the filtrate was concentrated in a reduced pressure. The obtained amorphous compound was recrystallized (ethyl acetate-ether-hexane) and it was dried with hot air at 50° C. overnight to give 68 mg of the title compound as a white crystal. Yield 85%.

1H-NMR (400 MHz, CDCl3) d; 7.40 (1H, brd, J=6.0 Hz), 5.35 (1H, dd, J=2.4, 6.8 Hz), 4.82 (1H, d, J=9.2 Hz), 4.55 (1H, m), 3.92 (1H, d, J=6.8 Hz), 3.77 (4H, t, J=4.4 Hz), 3.31 (2H, s), 3.28 (1H, dd, J=2.4, 11.6 Hz), 3.12 (1H, dd, J=6.8, 11.6 Hz), 2.62 (4H, m), 2.14–1.52 (7H, m), 1.17 (1H, m), 1.01 (3H, d, J=6.4 Hz), 1.00 (3H, d, J=6.8 Hz), 0.87 (3H, t, J=7.6 Hz).

Example 17

[3R-(3α, 6α, 9β, 9aβ)]-6-[[(2S, 4S)-1-Oxo-2-(4-thiomorpholinyl)acetylthio-3-methylpentyl]amino]-9methyl-5-oxo-octahydrothiazolo[3,2-a]azepine-3-carboxylic acid

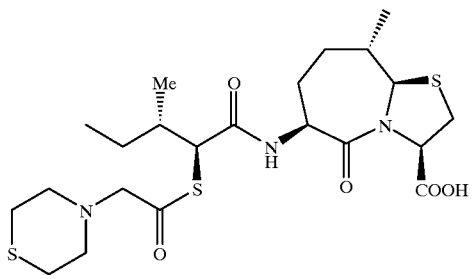

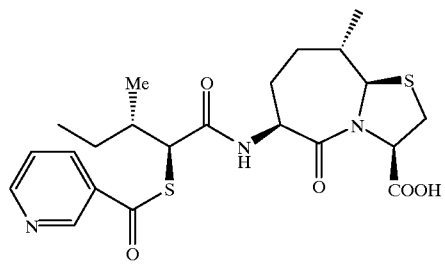

81 mg of the title compound was obtained as a white crystal from 70 mg (0.19 mmol) of the [3R-(3α, 6α, 9β, 9aβ)]-6-[[(2S, 3S)-1-oxo-2-thio-3-methylpentyl]amino]-9-methyl-5-oxo-octahydrothiazolo[3,2-a]azepine-3-carboxylic acid obtained in Example 3, 55 mg (0.28 mmol) of 4-thiomorpholinylacetic acid hydrochloride and 33 mg (0.21 mmol) of N,N'-carbodi-imidazole in a similar manner to that of Example 16. Yield 84%.

1H-NMR (400 MHz, CDCl3) d; 7.40 (1H, brd, J=6.4 Hz), 5.33 (1H, m), 4.83 (1H, d, J=9.6 Hz), 4.56 (1H, m), 3.89 (1H, d, J=7.2 Hz), 3.32–3.26 (1H, m), 3.30 (2H, s), 3.12 (1H, dd, J=6.4, 11.2 Hz), 2.88–2.82 (2H, m), 2.76–2.70 (2H, m), 2.14–1.90 (4H, m), 1.78–1.54 (3H, m), 1.18 (1H, m), 1.01 (3H, d, J=6.8 Hz), 1.00 (3H, d, J=6.4 Hz), 0.90 (3H, t, J=7.6 Hz).

Example 18

[3R-(3α, 6α, 9β, 9aβ)]-6-[[(2S, 3S)-1-Oxo-2-(4-dioxothiomorpholinyl)acetylthio-3-methylpentyl]amino]-9-methyl-5-oxo-octahydrothiazolo[3,2-a]azepine-3-carboxylic acid

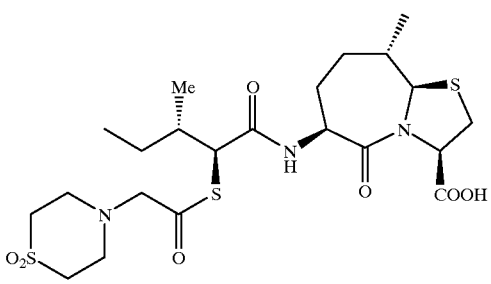

73 mg of the title compound was obtained as a white crystal from 70 mg (0.19 mmol) of the [3R-(3α, 6α, 9β, 9aβ)]-6-[[(2S, 3S)-1-oxo-2-thio-3-methylpentyl]amino]-9-methyl-5-oxo-octahydrothiazolo[3,2-a]azepine-3-carboxylic acid obtained in Example 3, 54 mg (0.28 mmol) of 4-dioxothiomorpholinylacetic acid and 33 mg (0.21 mmol) of N,N'-carbodiimidazole in a similar manner to that of Example 16. Yield 71%.

1H-NMR (400 MHz, CDCl3) d; 7.50 (1H, brd, J=6.4 Hz), 5.27 (1H, dd, J=3.2, 6.8 Hz), 4.81 (1H, d, J=9.6 Hz), 4.55 (1H, m), 3.96 (1H, d, J=6.4 Hz), 3.46 (2H, s), 3.27 (1H, dd, J=3.2, 12.0 Hz), 3.24–3.10 (5H, m), 2.18–1.92 (4H, m), 1.76–1.63 (2H, m), 1.55 (1H, m), 1.17 (1H, m), 1.01 (3H, d, J=6.8 Hz), 1.00 (3H, d, J=6.8 Hz), 0.90 (3H, t, J=7.6 Hz).

Example 19

[3R-(3α, 6α, 9β, 9aβ)]-6-[[(2S, 3S)-1-Oxo-9-nicotinoylthio-3-methylpentyl]amino]-9-methyl-5-oxo-octahydrothiazolo[3,2-a]azepine-3-carboxylic acid 28 mg of the title compound was obtained as a white crystal from 50 mg (0.13 mmol) of the [3R-(3α, 6α, 9β, 9aβ)]-6-[[(2S, 3S)-1-oxo-2-thio-3-methylpentyl]-amino]-9-methyl-5-oxo-octahydrothiazolo[3,2-a]-azepine-3-carboxylic acid obtained in Example 3, 18 mg (0.15 mmol) of nicotinic acid and 23 mg (0.14 mmol) of N,N'-carbodiimidazole in a similar manner to that of Example 12. Yield 44%.

1H-NMR (400 MHz, CDCl3) d; 9.17 (1H, br), 8.80 (1H, br), 8.22 (1H, brd, J=8.4 Hz), 7.58 (1H, br), 7.43 (1H, m), 5.27 (1H, br,), 4.82 (1H, br), 4.60 (1H, br), 4.23 (1H, brd, J=7.2 Hz), 3.34 (1H, br), 3.12 (1H, br), 2.24–1.92 (4H, m), 1.80–1.58 (3H, m), 1.24 (1H, m), 1.06 (3H, d, J=6.8 Hz), 1.00–0.84 (6H, m).

Example 20

[3R -(3α, 6α, 9α, 9aβ)]-6-[[(2S, 3S)-1-Oxo-2-acetylthio-3-methylpentyl]amino]-9-methyl-5-oxo-octahydrothiazolo[3,2-a]azepine-3-carboxylic acid

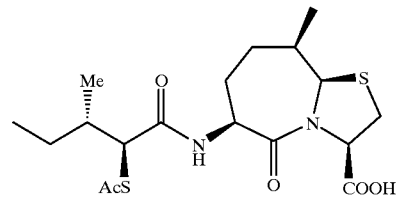

163 mg of the title compound was obtained as a white crystal from 212 mg (0.57 mmol) of the [3R-(3α, 6α, 9α, 9aβ)]-6-[[(2S, 3S)-1-oxo-2-thio-3-methylpentyl]amino]-9-methyl-5-oxo-octahydrothiazolo[3,2-a]azepine-3-carboxylic acid obtained in Example 11, 64 ml (0.68 mmol) of acetic anhydride and 22 mg (0.17 mmol) of anhydrous cobalt chloride in a similar manner to that of Example 12. Yield 69%.

1H-NMR (400 MHz, CDCl3) d; 7.30–7.20 (1H, m), 5.28 (1H, s), 5.08 (1H, dd, J=2.4, 6.4 Hz), 4.59 (1H, m), 3.95 (1H, d, J=7.2 Hz), 3.48 (1H, dd, J=2.4, 11.6 Hz), 3.12 (1H, dd, J=6.4, 11.6 Hz), 2.40 (3H, s), 2.16–1.52 (7H, m), 1.18 (1H, m), 1.01 (3H, d, J=6.4 Hz), 1.00 (3H, d, J=7.2 Hz), 0.91 (3H, t, J=7.2 Hz).

Example 21

[3R-(3α, 6α,9α, 9aβ)]-6-[[(2S, 3S)-1-Oxo-2-benzoylthio-3-methylpentyl]amino]-9-methyl-5-oxo-octahydrothiazolo[3,2-a]azepine-3-carboxylic acid

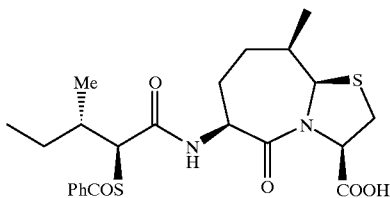

163 mg of the title compound was obtained as a white crystal from 265 mg (0.71 mmol) of the [3R-(3α, 6α, 9α, 9aβ)]-6-[[(2S, 3S)-1-oxo-2-thio-3-methylpentyl]amino]-9-methyl-5-oxo-octahydrothiazolo[3,2-a]azepine-3-carboxylic acid obtained in Example 11, 176 mg (0.78 mmol) of benzoic anhydride and 28 mg (0.21 mmol) of anhydrous cobalt chloride in a similar manner to that of Example 12. Yield 48%.

1H-NMR (400 MHz, CDCl3) d; 7.99 (2H, m), 7.60–7.40 (4H, m), 5.22 (1H, s), 5.03 (1H, br), 4.60 (1H, m), 4.08 (1H, br), 3.42 (1H, br), 3.03 (1H, br), 2.20–1.60 (7H, m), 1.24 (1H, m), 1.10–0.90 (9H, m).

Example 22

Methyl [3R-(3α, 6α, 9α, 9aβ)]-6-amino-9-ethyl-5-oxo-octahydrothiazolo[3,2-a]azepine-3-carboxylate

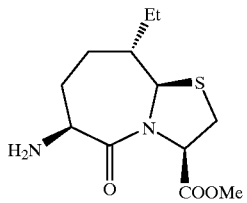

1.3 g (4.13 mmol) of the methyl [3R-(3α, 6α, 9β, 9aβ)]-6-acetylamino-9-ethyl-5-oxo-octahydrothiazolo[3,2-a]azepine-3-carboxylate obtained in Synthesis Example 19 was dissolved in a 10% solution (50 ml) of hydrochloric acid in methanol, followed by heating under reflux for two days. After it was distilled in a reduced pressure to remove the solvent, water was added thereto, followed by washing with dichloromethane. After the obtained aqueous layer was alkalified by adding a saturated aqueous solution of sodium hydrogencarbonate thereto, it was extracted with dichloromethane, followed by drying over anhydrous sodium sulfate. After filtration, the filtrate was concentrated in a reduced pressure to give 0.83 g of the title compound as a colorless oil. Yield 74%.

1H-NMR (400 MHz, CDCl3) d; 5.32 (1H, dd, J=3.5, 6.8 Hz), 4.89 (1H, d, J=9.2 Hz), 3.78 (3H, s), 3.55 (1H, dd, J=2.0, 10.5 Hz), 3.21 (1H, dd, J=3.5, 11.6 Hz), 3.09 (1H, dd, J=6.8, 11.6 Hz), 2.20–1.40 (9H, m), 0.92 (3H, t, J=7.6 Hz)

Example 23

Methyl [3R-(3α, 6α, 9β, 9aβ)]-6-[[(2S, 3S)-1-oxo-2-acetylthio-3-methylpentyl]amino]-9-ethyl-5-oxo-octahydrothiazolo[3,2-a]azepine-3-carboxylate

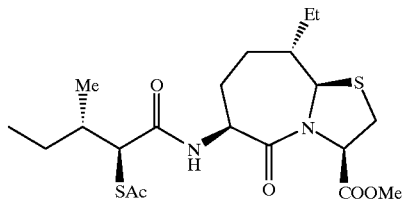

A solution of 0.70 g (3.66 mmol) of (2S, 3S)-2-acetylthio-3-methylpentanoic acid in tetrahydrofuran (50 ml) was added to 0.83 g (3.05 mmol) of the [3R-(3α, 6α, 9β, 9aβ)]-6-amino-9-ethyl-5-oxo-octahydrothiazolo[3,2-a]-azepine-3-carboxylate obtained in Example 22 under cooling with ice. To this solution, 0.70 g (3.66 mmol) of 1-ethyl-3-(3-dimethylaminopropyl) carbodiimide hydrochloride (DEC.HCl), 0.4 ml (3.66 mmol) of N-methylmorpholine and 0.50 g (9.3 mmol) of 1-hydroxy-1H-benzotriazole monohydrate (HOBT) were added successively, followed by stirring in a nitrogen atmosphere at room temperature for 18 hours. Water was added to the reaction solution and it was extracted with ethyl acetate. Then, the organic layer was washed with 1N-hydrochloric acid, a saturated aqueous solution of sodium hydrogencarbonate and a saturated aqueous solution of common salt, and dried over anhydrous magnesium sulfate. After filtration, the filtrate was concentrated in a reduced pressure and the obtained residue was purified by silica gel column chromatography (hexane:ethyl acetate=3:1) to give 476 mg of the title compound as a colorless oil. Yield 35%.

1H-NMR (400 MHz, CDCl3) d; 7.36 (1H, d, J=6.0 Hz), 5.34 (1H, dd, J=3.2, 6.4 Hz), 4.86 (1H, d, J=9.6 Hz), 4.54 (1H, m), 3.97 (1H, d, J=6.8 Hz), 3.78 (3H, s), 3.21 (1H, dd, J=3.2, 12.0 Hz), 3.11 (1H, dd, J=6.4, 12.0 Hz), 2.38 (3H, s), 2.16–2.04 (2H, m), 1.82–1.52 (6H, m), 1.31 (1H, m), 1.16 (1H, m), 0.99 (3H, d, J=6.4 Hz), 0.91 (3H, t, J=7.2 Hz), 0.88 (3H, t, J=7.2 Hz)

Example 24

[3R-3α, 6α, 9β, 9aβ)]-6-[[(2S, 3S)-1-Oxo-2-thio-3-methylpentyl]amino]-9-ethyl-5-oxo-octahydrothiazolo[3,2-a]azepine-3-carboxylic acid

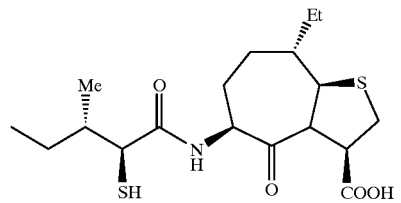

476 mg (1.07 mmol) of the methyl [3R-(3α, 6α, 9β, 9aβ)]-6-[[(2S, 3S)-1-oxo-2-acetylthio-3-methylpentyl] amino]-9-ethyl-5-oxo-octahydrothiazolo[3,2-a]azepine-3-carboxylate obtained in Example 23 was dissolved in 10.7 ml of deaerated ethanol and 5.36 ml of a deaerated 1N-aqueous solution of lithium hydroxide was added thereto under cooling with ice, followed by stirring in a nitrogen atmosphere at room temperature for one hour. The reaction solution was acidified by adding 2N-hydrochloric acid thereto under cooling with ice and diluted with water, followed by the extraction with dichloromethane. The organic layer was washed with a saturated aqueous solution of common salt, and dried over anhydrous magnesium sulfate. After filtration, the filtrate was concentrated in a reduced pressure. The obtained amorphous was triturated with hexane, followed by the collection by filtration. This was dried with hot air at 50° C. for 12 hours to give 300 mg of the title compound. Yield 72%.

1H-NMR (400 MHz, CDCl3) d; 7.66 (1H, d, J=6.4 Hz), 5.36 (1H, dd, J=3.2, 6.4 Hz), 4.91 (1H, d, J=9.2 Hz), 4.61 (1H, m), 3.28 (1H, dd, J=3.2, 12.0 Hz), 3.22 (1H, dd, J=6.8, 8.8 Hz), 3.13 (1H, dd, J=6.4, 12.0 Hz), 2.16–2.08 (2H, m), 1.98 (1H, m), 1.87 (1H, d, J=8.8 Hz), 1.84–1.56 (5H, m), 1.38–1.18 (2H, m), 0.99 (3H, d, J=6.4 Hz), 0.93 (3H, t, J=7.2 Hz), 0.90 (3H, t, J=7.6 Hz)

We claim:

1. A process for the preparation of a 6-aminothiazolo(3,2-a)azepine derivative comprising the step of electrolytically oxidizing a pipecolic acid derivative represented by the general formula (2):

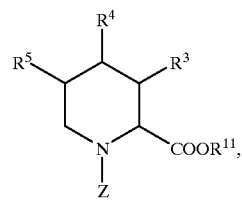

(2)

wherein $R^3$, $R^4$ and $R^5$ each independently represent a hydrogen atom, a hydroxyl group, a lower alkyl group, a lower alkoxyl group, a lower alkylthio group, an aryl group which may be substituted or a heteroaryl group which may be substituted; $R^{11}$ represents a protecting group of a carboxylic acid; and Z represents an acyl group, to give a hemiacetal represented by the general formula (3):

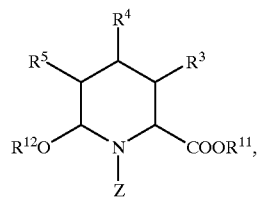

(3)

$R^3$, $R^4$, $R^5$ and $R^{11}$ having the meanings as described above; and wherein $R^{12}$ represents a hydrogen atom or a linear or branched alkyl group having 1 to 6 carbon atoms.

2. A process for the preparation of a 6-aminothiazolo(3,2-a)azepine derivative as set forth in claim 1, comprising the step of reacting a hemiacetal represented by the general formula (3):

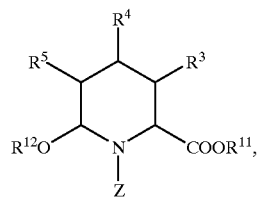

(3)

$R^3$, $R^4$ and $R^5$ each independently representing a hydrogen atom, a hydroxyl group, a lower alkyl group, a lower alkoxyl group, a lower alkylthio group, an aryl group, which may be substituted, or a heteroaryl group, which may be substituted; $R^{11}$ representing a protecting group of a carboxylic acid; and wherein $R^{12}$ represents a hydrogen atom or a linear or branched alkyl group having 1 to 6 carbon atoms, with a cysteine derivative represented by the general formula (4):

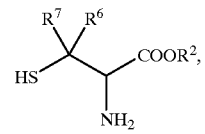

(4)

wherein $R^2$ represents a hydrogen atom or a protecting group of a carboxylic acid; and $R^6$ and $R^7$ each independently represent a hydrogen atom, a lower alkyl group or an arylalkyl group, which may be substituted, to give a thiazolidine derivative represented by the general formula (5):

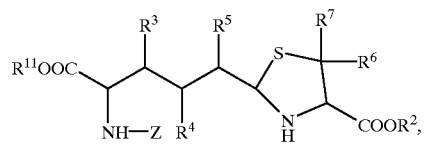

(5)

wherein $R^2$ represents a protecting group of a carboxylic acid; $R^6$ and $R^7$ each independently represent a hydrogen atom, a lower alkyl group or an arylalkyl group, which may be substituted; $R^3$, $R^4$ and $R^5$ each independently represent a hydrogen atom, a hydroxyl group, a lower alkyl group, a lower alkoxyl group, a lower alkylthio group, an aryl group, which may be substituted, or a heteroaryl group, which may be substituted; $R^{11}$ represents a protecting group of a carboxylic acid; and Z represents an acyl group, cyclizing a thiazolidine derivative obtained by further deprotecting the derivative of formula (5) and represented by the general formula (6):

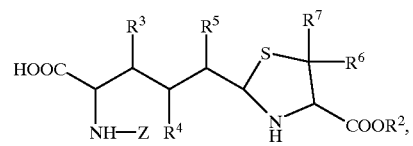

(6)

wherein $R^2$, $R^3$, $R^4$, $R^5$, $R^6$, $R^7$ and Z have the meanings as described above, to give an amino acid derivative represented by the general formula (7):

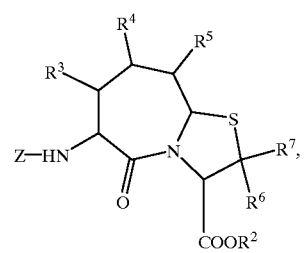

(7)

wherein $R^2$, $R^3$, $R^4$, $R^5$, $R^6$, $R^7$ and Z have the meanings as described above, and, if necessary, deprotecting the derivative of formula (7) to give an amino acid derivative represented by the general formula (1):

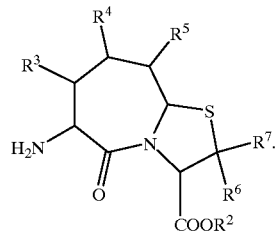
(1)

3. A process for the preparation of a 6-aminothiazolo(3, 2-a)azepine derivative as set forth in claim 1, comprising the steps of electrolytically oxidizing a pipecolic acid derivative represented by the general formula (2):

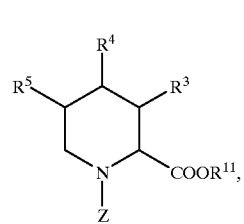
(2)

to give a hemiacetal represented by the general formula (3):

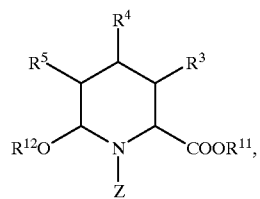
(3)

$R^3$, $R^4$ and $R^5$ each independently representing a hydrogen atom, a hydroxyl group, a lower alkyl group, a lower alkoxyl group, a lower alkylthio group, an aryl group, which may be substituted, or a heteroaryl group, which may be substituted; and $R^{11}$ represents a protecting group of a carboxylic acid; and wherein $R^{12}$ represents a hydrogen atom or a linear or branched alkyl group having 1 to 6 carbon atoms, reacting the hemiacetal (3) with a cysteine derivative represented by the general formula (4):

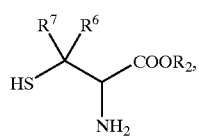
(4)

wherein $R^2$ represents a hydrogen atom or a protecting group of a carboxylic acid; and $R^6$ and $R^7$ each independently represent a hydrogen atom, a lower alkyl group or an arylalkyl group, which may be substituted, to give a thiazolidine derivative represented by the general formula (5):

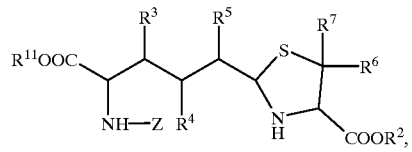
(5)

wherein $R^2$ represents a protecting group of a carboxylic acid; $R^6$ and $R^7$ each independently represent a hydrogen atom, a lower alkyl group or an arylalkyl group, which may be substituted; $R^3$, $R^4$ and $R^5$ each independently represent a hydrogen atom, a hydroxyl group, a lower alkyl group, a lower alkoxyl group, a lower alkylthio group, an aryl group, which may be substituted, or a heteroaryl group, which may be substituted; $R^{11}$ represents a protecting group of a carboxylic acid; and Z represents an acyl group, cyclizing a thiazolidine derivative obtained by further deprotecting the derivative of formula (5) and represented by the general formula (6):

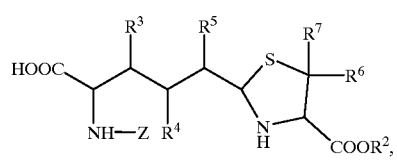
(6)

wherein $R^3$, $R^4$, $R^5$, $R^6$, $R^7$, $R^2$ and Z have the meanings as described above,
to give an amino acid derivative represented by the general formula (7):

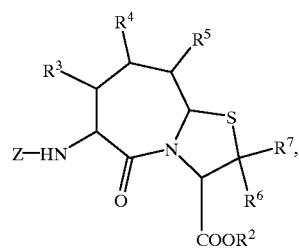
(7)

wherein $R^3$, $R^4$, $R^5$, $R^6$, $R^7$, $R^2$ and Z have the meanings as described above,
and, if necessary, deprotecting the derivative of general formula (7) to give an amino acid derivative represented by the general formula (1):

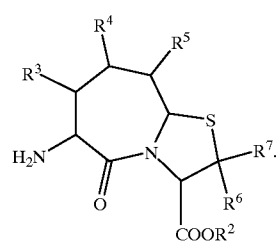
(1)

4. A process for the preparation of a 6-aminothiazolo(3, 2-a)azepine derivative comprising the steps of electrolytically oxidizing a pipecolic acid derivative represented by the general formula (2a):

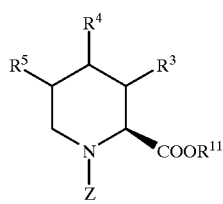
(2a)

to give a hemiacetal represented by the general formula (3a):

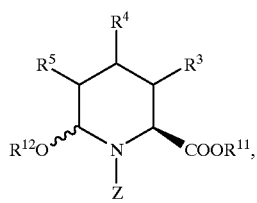
(3a)

wherein $R^3$, $R^4$ and $R^5$ each independently represent a hydrogen atom, a hydroxyl group, a lower alkyl group, a lower alkoxyl group, a lower alkylthio group, an aryl group, which may be substituted, or a heteroaryl group, which may be substituted; $R^{11}$ represents a protecting group of a carboxylic acid; Z represents an acyl group; and wherein $R^{12}$ represents a hydrogen atom or a linear or branched alkyl group having 1 to 6 carbon atoms.

5. A process for the preparation of a 6-aminothiazolo(3,2-a)azepine derivative comprising the steps of reacting a hemiacetal represented by the general formula (3a):

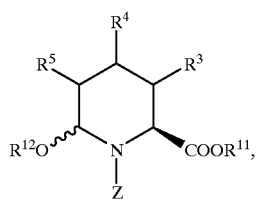
(3a)

wherein $R^3$, $R^4$ and $R^5$ each independently represent a hydrogen atom, a hydroxyl group, a lower alkyl group, a lower alkoxyl group, a lower alkylthio group, an aryl group, which may be substituted, or a heteroaryl group, which may be substituted; $R^{11}$ represents a protecting group of a carboxylic acid; Z represents an acyl group; and wherein $R^{12}$ represents a hydrogen atom or a linear or branched alkyl group having 1 to 6 carbon atoms,
with a cysteine derivative represented by the general formula (4a):

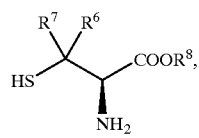
(4a)

wherein $R^8$ represents a hydrogen atom or a protecting group of a carboxylic acid; and $R^6$ and $R^7$ each independently represent a hydrogen atom, a lower alkyl group or an arylalkyl group, which may be substituted, to give a thiazolidine derivative (5a):

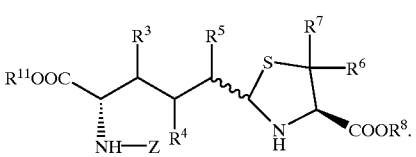
(5a)

6. A process for the preparation of the 6-aminothiazolo (3,2-a)azepine derivative as set forth in claim 4, comprising the steps of reacting a hemiacetal represented by the general formula (3a):

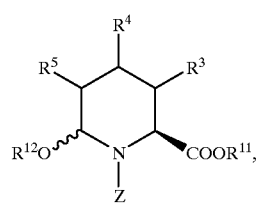
(3a)

wherein $R^3$, $R^4$ and $R^5$ each independently represent a hydrogen atom, a hydroxyl group, a lower alkyl group, a lower alkoxyl group, a lower alkylthio group, an aryl group, which may be substituted, or a heteroaryl group, which may be substituted; $R^{11}$ represents a protecting group of a carboxylic acid; Z represents an acyl group; and wherein $R^{12}$ represents a hydrogen atom or a linear or branched alkyl group having 1 to 6 carbon atoms,
with a cysteine derivative represented by the general formula (4a):

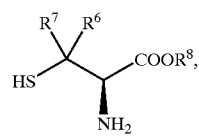
(4a)

wherein $R^8$ represents a hydrogen atom or a protecting group of a carboxylic acid; and $R^6$ and $R^7$ each independently represent a hydrogen atom, a lower alkyl group or an arylalkyl group, which may be substituted, to give a thiazolidine derivative represented by the general formula (5a):

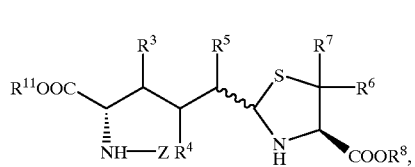
(5a)

wherein $R^8$ represents a hydrogen atom or a protecting group of a carboxylic acid; $R^6$ and $R^7$ each independently represent a hydrogen atom, a lower alkyl group or an arylalkyl group, which may be substituted; $R^3$, $R^4$ and $R^5$ each independently represent a hydrogen atom, a hydroxyl group, a lower alkyl group, a lower alkoxyl group, a lower alkylthio group, an aryl group, which may be substituted, or a heteroaryl group, which may be substituted; $R^{11}$ represents a protecting group of a carboxylic acid; and Z represents an acyl group, cyclizing a thiazolidine derivative obtained by further deprotecting the derivative of formula (5a) and represented by the general formula (6a):

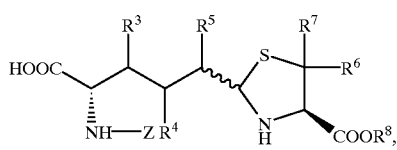

(6a)

wherein $R^3$, $R^4$, $R^5$, $R^6$, $R^7$, $R^8$ and Z have the meanings as described above, to give an amino acid derivative represented by the general formula (7a):

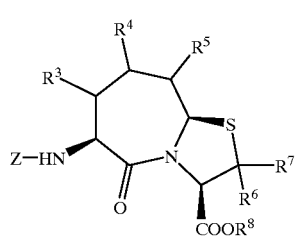

(7a)

and, if necessary, deprotecting the derivative of formula (7a) to give an amino acid derivative represented by the general formula (1a):

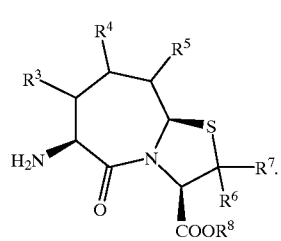

(1a)

7. A process for the preparation of the 6-aminothiazolo (3,2-a)azepine derivative as set forth in claim 4, comprising the steps of electrolytically oxidizing a pipecolic acid derivative represented by the general formula (2a):

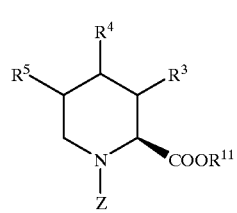

(2a)

to give a hemiacetal represented by the general formula (3a):

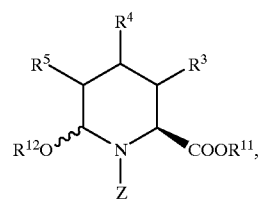

(3a)

wherein $R^3$, $R^4$ and $R^5$ each independently represent a hydrogen atom, a hydroxyl group, a lower alkyl group, a lower alkoxyl group, a lower alkylthio group, an aryl group, which may be substituted, or a heteroaryl group, which may be substituted; Z represents an acyl group; $R^{11}$ represents a protecting group of a carboxylic acid; and wherein $R^{12}$ represents a hydrogen atom or a linear or branched alkyl group having 1 to 6 carbon atoms, reacting the hemiacetal (3a) obtained with a cysteine derivative represented by the general formula (4a):

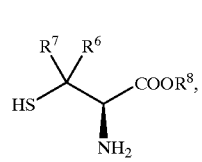

(4a)

wherein $R^8$ represents a hydrogen atom or a protecting group of a carboxylic acid; and $R^6$ and $R^7$ each independently represent a hydrogen atom, a lower alkyl group or an arylalkyl group, which may be substituted, to give a thiazolidine derivative represented by the general formula (5a):

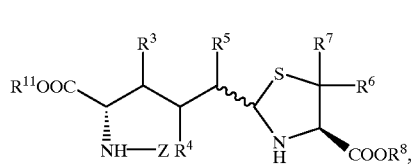

(5a)

wherein $R^8$ represents a hydrogen atom or a protecting group of a carboxylic acid; $R^6$ and $R^7$ each independently represent a hydrogen atom, a lower alkyl group or an arylalkyl group, which may be substituted; $R^3$, $R^4$ and $R^5$ each independently represent a hydrogen atom; a hydroxyl group, a lower alkyl group, a lower alkoxyl group, a lower alkylthio group, an aryl group, which may be substituted, or a heteroaryl group, which may be substituted; $R^{11}$ represents a protecting group of a carboxylic acid; and Z represents an acyl group, cyclizing a thiazolidine derivative obtained by further deprotecting the above derivative and represented by the general formula (6a):

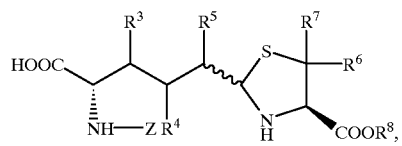

(6a)

wherein $R^3$, $R^4$, $R^5$, $R^6$, $R^7$, $R^8$ and Z have the meanings as described above,
to give an amino acid derivative represented by the general formula (7a):

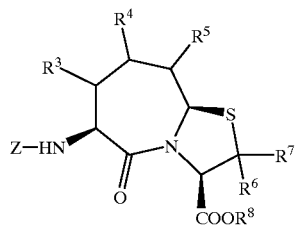

(7a)

and, if necessary, deprotecting the derivative of formula (7a) to give an amino acid derivative represented by the general formula (1a):

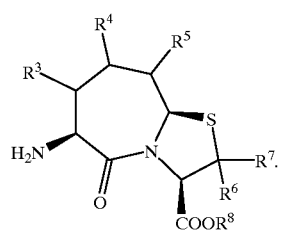

(1a)

8. A process for the preparation of a (2S, 3S)-3-methyl-2-thiopentanoic acid derivative represented by the general formula (8):

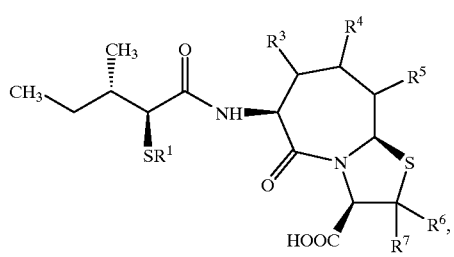

(8)

wherein $R^1$ represents a hydrogen atom or an acyl group; comprising a step of synthesizing an α-hydroxycarboxylicamide derivative represented by the general formula (12):

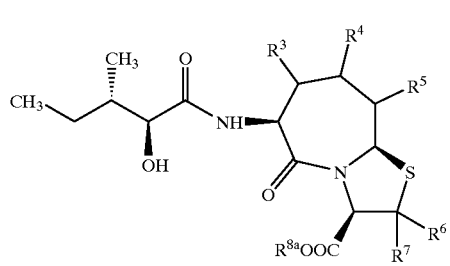

(12)

by coupling an α-hydroxycarboxylic acid (10):

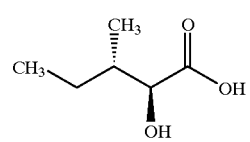

(10)

with an amine derivative represented by the general formula (11):

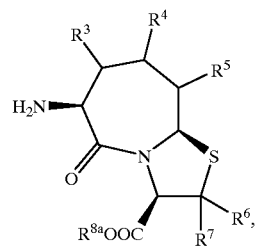

(11)

wherein $R^3$, $R^4$ and $R^5$ each independently represent a hydrogen atom, a lower alkyl group, a lower alkoxyl group, a lower alkylthio group, an aryl group, which may be substituted, or a heteroaryl groups which may be substituted; $R^6$ and $R^7$ each independently represent a hydrogen atom, a lower alkyl group, an aryl group, which may be substituted, or an arylalkyl group, which may be substituted; and $R^{8a}$ represents a protecting group of a carboxylic acid.

9. A process for the preparation of a (2S, 3S)-3-methyl-2-thiopentanoic acid derivative represented by the general formula (8):

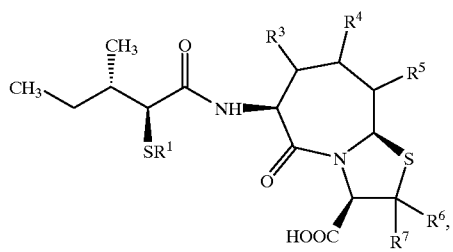
(8)

wherein R¹ represents a hydrogen atom or an acyl group;, comprising a step of hydroxylating L-isoleucine (9):

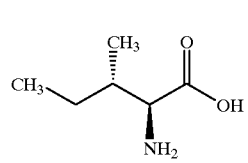
(9)

to give an α-hydroxycarboxylic acid (10):

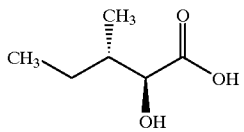
(10)

and coupling the acid (10) with an amine derivative represented by the general formula (11):

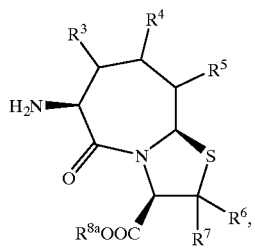
(11)

wherein $R^3$, $R^4$ and $R^5$ each independently represent a hydrogen atom, a lower alkyl group, a lower alkoxyl group, a lower alkylthio group, an aryl group, which may be substituted, or a heteroaryl group, which may be substituted; $R^6$ and $R^7$ each independently represent a hydrogen atom, a lower alkyl group, an aryl group, which may be substituted, or an arylalkyl group, which may be substituted; and $R^{8a}$ represents a protecting group of a carboxylic acid, to synthesize an α-hydroxycarboxylic amide derivative represented by the general formula (12):

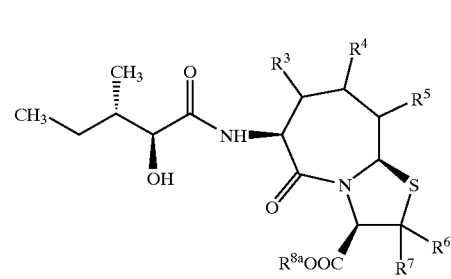
(12)

10. A process for the preparation of a (2S, 3S)-3-methyl-2-thiopentanoic acid derivative represented by the general formula (8):

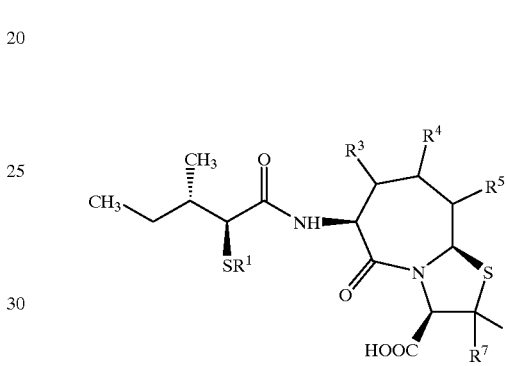
(8)

wherein $R^1$ represents a hydrogen atom or an acyl group; $R^3$, $R^4$ and $R^5$ each independently represent a hydrogen atom, a hydroxyl group, a lower alkyl group, a lower alkoxyl group, a lower alkylthio group, an aryl group, which may be substituted, or a heteroaryl group, which may be substituted; and $R^6$ and $R^7$ each independently represent a hydrogen atom, a lower alkyl group or an arylalkyl group, which may be substituted; from an α-hydroxycarboxylic amide derivative represented by the general formula (12):

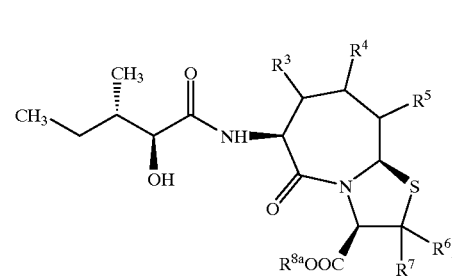
(12)

wherein $R^{8a}$ is a protecting group for a carboxylic acid, comprising a step of halogenating the α-hydroxycarboxylic amide derivative (12) to give an α-halocarboxylic amide derivative represented by the general formula (13):

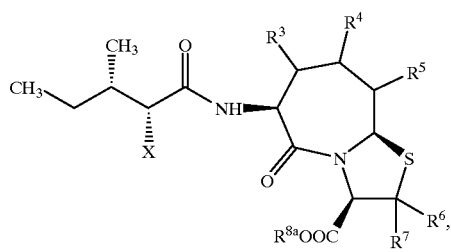
(13)
if necessary, hydrolyzing the α-halocarboxylic amide derivative of general formula (13) to give an α-halocarboxylic acid derivative represented by the general formula (14):
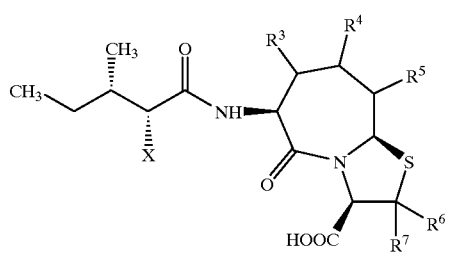
(14)
and, further, introducing an acylthio group thereinto.
* * * * *

UNITED STATES PATENT AND TRADEMARK OFFICE
CERTIFICATE OF CORRECTION

PATENT NO : 6 051 705
DATED : April 18, 2000
INVENTORS : Hitoshi OINUMA et al It is certified that error appears in the above-identified patent and that said Letters Patent are hereby corrected as shown below:

Column 64, Line 56; change "a heteroaryl groups"
to ---a heteroaryl group,---.

Signed and Sealed this

Tenth Day of April, 2001

Attest:

NICHOLAS P. GODICI

Attesting Officer     Acting Director of the United States Patent and Trademark Office